US008814856B2

(12) United States Patent  (10) Patent No.: US 8,814,856 B2
Elmouelhi et al.  (45) Date of Patent: Aug. 26, 2014

(54) EXTENSION AND RETRACTION MECHANISM FOR A HAND-HELD DEVICE

(75) Inventors: Ahmed Elmouelhi, Minneapolis, MN (US); Steven C. Christian, New Brighton, MN (US)

(73) Assignee: Medtronic, Inc., Minneapolis, MN (US)

( * ) Notice: Subject to any disclaimer, the term of this patent is extended or adjusted under 35 U.S.C. 154(b) by 1788 days.

(21) Appl. No.: 11/799,115

(22) Filed: Apr. 30, 2007

(65) Prior Publication Data

US 2008/0269862 A1  Oct. 30, 2008

(51) Int. Cl.
*A61B 18/18* (2006.01)

(52) U.S. Cl.
USPC .................. 606/41; 606/45; 606/46; 607/101

(58) Field of Classification Search
USPC .................. 606/45–46, 50–52; 607/101–102; 604/21–22
See application file for complete search history.

(56) References Cited

U.S. PATENT DOCUMENTS

| | | | |
|---|---|---|---|
| 2,784,603 A * | 3/1957 | Collins | ........................... 74/169 |
| 3,144,020 A | 8/1964 | Zingale | |
| 5,370,675 A | 12/1994 | Edwards et al. | |
| 5,383,874 A | 1/1995 | Jackson et al. | |
| 5,400,267 A | 3/1995 | Denen et al. | |
| 5,435,805 A | 7/1995 | Edwards et al. | |
| 5,454,782 A | 10/1995 | Perkins | |
| 5,458,597 A | 10/1995 | Edwards et al. | |
| 5,470,308 A | 11/1995 | Edwards et al. | |
| 5,472,441 A | 12/1995 | Edwards et al. | |
| 5,507,743 A | 4/1996 | Edwards et al. | |
| 5,531,676 A | 7/1996 | Edwards et al. | |
| 5,536,267 A | 7/1996 | Edwards et al. | |
| 5,651,780 A | 7/1997 | Jackson et al. | |
| 5,762,626 A | 6/1998 | Lundquist et al. | |

(Continued)

FOREIGN PATENT DOCUMENTS

| | | |
|---|---|---|
| EP | 1 201 196 | 5/2002 |
| GB | 2 269 538 A | 2/1994 |
| WO | WO 93/25136 | 12/1993 |
| WO | WO 01/05318 A1 | 1/2001 |

OTHER PUBLICATIONS

Birch et al., "Transurethral Resection of Prostate Under Sedation and Local Anesthesia (Sedoanalgesia)," Urology, Aug. 1991 vol. XXXVIII, No. 2., pp. 113-118.

(Continued)

*Primary Examiner* — Jaymi Della
(74) *Attorney, Agent, or Firm* — Shumaker & Sieffert, P.A.

(57) ABSTRACT

The disclosure describes a hand-held device that utilizes a mechanical lever system to operate the device with a single hand. The mechanical lever system is coupled to a sliding element within the housing of the hand-held device that slides linearly. The sliding element may be attached to another element that is extended, retracted, or rotated in or out of the device. For example, the hand-held device may be used for prostate ablation therapy. The hand-held device may include an ablation needle electrode that is extended out of a catheter and into a tissue of a patient by depressing an extension lever of the mechanical lever system to deliver ablation therapy. Depressing a retraction lever of the mechanical lever system may retract the needle electrode back into the catheter of the hand-held device. Other variations of the mechanical system and applications of the hand-held device are also described.

16 Claims, 15 Drawing Sheets

(56) References Cited

U.S. PATENT DOCUMENTS

| | | | |
|---|---|---|---|
| 5,807,309 | A | 9/1998 | Lundquist et al. |
| 5,839,011 | A | 11/1998 | Urasaki et al. |
| 5,865,788 | A | 2/1999 | Edwards et al. |
| 5,964,756 | A | 10/1999 | McGaffigan et al. |
| 5,995,875 | A | 11/1999 | Blewett et al. |
| 6,071,280 | A | 6/2000 | Edwards et al. |
| 6,077,244 | A | 6/2000 | Botich et al. |
| 6,090,105 | A | 7/2000 | Zepeda et al. |
| 6,106,521 | A | 8/2000 | Blewett et al. |
| 6,113,594 | A | 9/2000 | Savage |
| 6,113,597 | A | 9/2000 | Eggers et al. |
| 6,129,726 | A | 10/2000 | Edwards et al. |
| 6,165,169 | A | 12/2000 | Panescu et al. |
| 6,221,071 | B1 | 4/2001 | Sherry et al. |
| 6,231,591 | B1 | 5/2001 | Desai |
| 6,238,393 | B1 | 5/2001 | Mulier et al. |
| 6,241,702 | B1 | 6/2001 | Lundquist et al. |
| 6,302,903 | B1 | 10/2001 | Mulier et al. |
| 6,315,777 | B1 | 11/2001 | Comben |
| 6,327,492 | B1 | 12/2001 | Lemelson |
| 6,387,092 | B1 | 5/2002 | Burnside et al. |
| 6,391,027 | B1 | 5/2002 | Farin et al. |
| 6,402,742 | B1 | 6/2002 | Blewett et al. |
| 6,409,722 | B1 | 6/2002 | Hoey et al. |
| 6,419,690 | B1 | 7/2002 | Mikus et al. |
| 6,440,127 | B2 | 8/2002 | McGovern et al. |
| 6,461,296 | B1 | 10/2002 | Desai |
| 6,464,661 | B2 | 10/2002 | Edwards et al. |
| 6,471,698 | B1 | 10/2002 | Edwards et al. |
| 6,497,705 | B2 | 12/2002 | Comben |
| 6,514,247 | B1 | 2/2003 | McGaffigan et al. |
| 6,526,320 | B2 | 2/2003 | Mitchell |
| 6,537,248 | B2 | 3/2003 | Mulier et al. |
| 6,537,272 | B2 | 3/2003 | Christopherson et al. |
| 6,551,300 | B1 | 4/2003 | McGaffigan |
| 6,611,793 | B1 | 8/2003 | Burnside et al. |
| 6,623,515 | B2 | 9/2003 | Mulier et al. |
| 6,632,221 | B1 | 10/2003 | Edwards et al. |
| 6,632,222 | B1 | 10/2003 | Edwards et al. |
| 6,638,275 | B1 | 10/2003 | McGaffigan et al. |
| 6,641,580 | B1 | 11/2003 | Edwards et al. |
| 6,652,516 | B1 | 11/2003 | Gough |
| 6,685,648 | B2 | 2/2004 | Flaherty et al. |
| 6,706,039 | B2 | 3/2004 | Mulier et al. |
| 6,761,715 | B2 | 7/2004 | Carroll |
| 6,814,712 | B1 | 11/2004 | Edwards et al. |
| 6,989,004 | B2 | 1/2006 | Hinchliffe et al. |
| 7,261,709 | B2 | 8/2007 | Swoyer et al. |
| 7,261,710 | B2 | 8/2007 | Elmouelhi et al. |
| 2001/0031941 | A1 | 10/2001 | Edwards et al. |
| 2001/0039415 | A1 | 11/2001 | Francischelli et al. |
| 2002/0002393 | A1 | 1/2002 | Mitchell |
| 2002/0058933 | A1 | 5/2002 | Christopherson et al. |
| 2002/0111619 | A1 | 8/2002 | Keast et al. |
| 2002/0120260 | A1 | 8/2002 | Morris et al. |
| 2002/0120261 | A1 | 8/2002 | Morris et al. |
| 2002/0151884 | A1 | 10/2002 | Hoey et al. |
| 2002/0177846 | A1 | 11/2002 | Mulier et al. |
| 2002/0183740 | A1 | 12/2002 | Edwards et al. |
| 2003/0028188 | A1 | 2/2003 | Paddock et al. |
| 2003/0073989 | A1 | 4/2003 | Hoey et al. |
| 2003/0103932 | A1 | 6/2003 | Slepian et al. |
| 2004/0002647 | A1 | 1/2004 | Desai |
| 2004/0133194 | A1 | 7/2004 | Eum et al. |
| 2004/0147917 | A1 | 7/2004 | Mueller, Jr. et al. |
| 2004/0172112 | A1 | 9/2004 | Cioanta et al. |
| 2005/0288664 | A1* | 12/2005 | Ford et al. .................. 606/41 |
| 2007/0049929 | A1* | 3/2007 | Catanese et al. ............ 606/46 |

OTHER PUBLICATIONS

Leveillec et al., "Radiofrequency Interstitial Tissue Ablation: Wet Electrode," Journal of Endourology, vol. 17, No. 8, pp. 563-577, 2003.

Related patent application entitled "Delivery of Fluid During Transurethral Prostate Treatment", U.S. Appl. No. 10/424,040, filed Apr. 24, 2003, now abandoned.

Related patent application entitled "Bipolar Virtual Electrode for Transurethral Needle Ablation", U.S. Appl. No. 10/835,193, filed Apr. 29, 2004, now abandoned.

Related patent application entitled "Transurethral Needle Ablation System", U.S. Appl. No. 11/833,107, filed Aug. 2, 2007, Elmouelhi et al.

Notification of Transmittal of the International Search Report and the Written Opinion of the Internatinal Searching Authority, or the Declaration, for corresponding patent application No. PCT/US2008/054196, mailed Jun. 10, 2008, 10 pages.

* cited by examiner

EXTENSION AND RETRACTION MECHANISM FOR A HAND-HELD DEVICE

TECHNICAL FIELD

The invention relates to lever mechanisms and, more particularly, to mechanisms for extending and retracting elements.

BACKGROUND

Hand-held devices are commonly used to simplify certain actions performed by a user. The hand-held devices may have a handle and a trigger to translate user hand movement into an action. For example, hand-held devices may be used in applications such as toys, gardening equipment, fastening tools, cooking utensils, manufacturing equipment, and medical devices. In medical device applications, the physician may diagnose or treat a patient condition with the hand-held device to simplify the medical operation. The hand-held device may utilize a mechanically or electrically actuated mechanism that performs the action.

One hand-held device may be used by a clinician to treat benign prostate hyperplasia (BPH) in men. BPH is a condition caused by a second period of continued prostate gland growth that constricts the urethra and may cause problems with urination and bladder functionality. The location of the prostate allows for the urethra to be used as an access point to reach the prostate and treat the patient. Minimally invasive techniques for treating BPH include inserting a needle attached to the hand-held device through the urethra to place the needle at the prostate site. The hand-held device may be used to insert the needle and provide a therapeutic energy for prostate ablation. A single trigger of the hand-held device may be used to extend the needle into the prostate. The needle applies energy to ablate the prostate tissue and reduce the tissue volume of the prostate. After ablation is completed, the user may have to use two hands to pull the trigger away from the handle of the hand-held device in order to retract the needle back into the device before removing the device from the patient.

SUMMARY

The disclosure describes a hand-held device that utilizes a mechanical lever system to operate the device with a single hand. The mechanical lever system is coupled to a sliding element that slides linearly within the housing of the hand-held device. The sliding element may be attached to another element that is extended, retracted, or rotated in or out of the device. One or more levers that extend from the housing of the held-held device are operated with fingers of the user to perform tasks with the device. A single-handed device may allow the second hand of the user to be free for performing other tasks simultaneously.

For example, the hand-held device may be used for prostate ablation therapy. The hand-held device may include an ablation needle electrode that is extended out of a catheter and into a tissue of a patient by depressing an extension lever of the mechanical lever system to deliver ablation therapy. Depressing a retraction lever of the mechanical lever system may retract the needle electrode back into the catheter of the hand-held device. In this manner, the hand-held device may be appropriate for performing delicate actions of ablation therapy on tissues of the patient. Other variations of the mechanical system and applications of the hand-held device are also described.

In one embodiment, the disclosure is directed to a device that includes a housing configured to be held in the hand of a user, a sliding element that slides within the housing, and an extension lever coupled to the sliding element. The extension lever moves the sliding element in a first direction when the extension lever is moved in a second direction. The device also includes a retraction lever coupled to the sliding element. The retraction lever moves the sliding element in the second direction when the retraction lever is moved in the second direction.

In another embodiment, the disclosure is directed to a device that includes a housing configured to be held in a hand of a user and a sliding element that moves within the housing. The device also includes an extension lever that partially resides within the housing and pivots about an extension pivot point attached to the housing. The extension lever is coupled to the sliding element via an extension link, and a first end of the extension link pivots about an extension link pivot point located at a first end of the extension lever and a second end of the extension link pivots about a block pivot point attached to the sliding element. The device also includes a retraction lever that partially resides within the housing and is coupled to the sliding element.

In an alternative embodiment, the disclosure is directed to a system that includes a generator that produces radio frequency energy for ablation and a hand-held device coupled to the generator. The hand-held device includes a housing configured to be held in a hand of a user and an ablation needle that slides within a catheter coupled to the housing, wherein the ablation needle is coupled to the generator. The hand-held device also includes an extension lever that pivots about an extension pivot point attached to the housing, wherein the extension lever is coupled to the ablation needle and moves the ablation needle in a first direction, and a retraction lever coupled to the ablation needle that moves the ablation needle in a second direction.

In various embodiments, the hand-held device may provide one or more advantages. For example, the user may extend and retract an ablation needle electrode by using only one hand. The hand-held device allows the user to perform both extension and retraction of the needle electrode by using the ergonomic squeezing function of either the right or left human hand. This single-handed operation may allow the user to perform additional tasks with the user's other free hand. The hand-held device also allows the user to accurately control each extension and retraction movement without uncontrolled mechanical devices such as springs or torque members. In addition, the hand-held device allows the user to extend and retract the needle electrode multiple times without having to reset or adjust any other component of the device.

The details of one or more embodiments of the invention are set forth in the accompanying drawings and the description below. Other features, objects, and advantages of the invention will be apparent from the description and drawings, and from the claims.

DETAILED DESCRIPTION

Hand-held devices are commonly employed in a variety of applications that require a user to manually perform a function. The hand-held device may benefit the user by including a component shaped to access a specific location or a component that provides a mechanical or electrical advantage to performing the function. The hand-held device may include a lever, trigger, button, or some other type of mechanism that allows the user to use the hand-held device with one or more fingers and/or a thumb. Hand-held devices may be used in applications that include toys, gardening equipment, fastening tools, kitchen utensils, manufacturing equipment and medical devices. The hand-held device described herein is particularly well suited for use in medical devices, but the mechanism is not limited to use in medical device applications. The hand-held device is described only in terms of a medical device for the sake of simplicity.

As described in more detail below, the hand-held device is embodied as a medical device for ablating prostate tissue. The hand-held device includes a housing that a user, such as a clinician or a physician, holds in one hand. A catheter, e.g., an elongated housing with a lumen, resides partially within the housing and includes an ablation needle that may be extended out from the catheter to penetrate the prostate of the patient and then retracted back into the catheter. In order to extend and retract the ablation needle, the hand-held device includes a mechanical lever system that enables the user to extend and retract the ablation needle with only the one hand that is holding the housing.

The mechanical lever system includes rotating and sliding components that extend and retract the needle by squeezing a lever of the lever system against the handle of the housing. The mechanical lever system may include an extension lever and a retraction lever that each extend from the housing next to the handle to allow the user to squeeze the appropriate lever. The extension and retraction levers move in opposite directions from each other during needle extension and retraction. For example, squeezing the extension lever forces the ablation needle to extend from the catheter and also moves the retraction lever away from the handle. Once the retraction lever is away from the handle, it may be squeezed against the handle to retract the ablation needle back into the catheter and move the extension lever away from the handle to its original position. Multiple embodiments of the mechanical lever system may be employed to extend and retract the ablation needle, as discussed further below.

Figure 1:
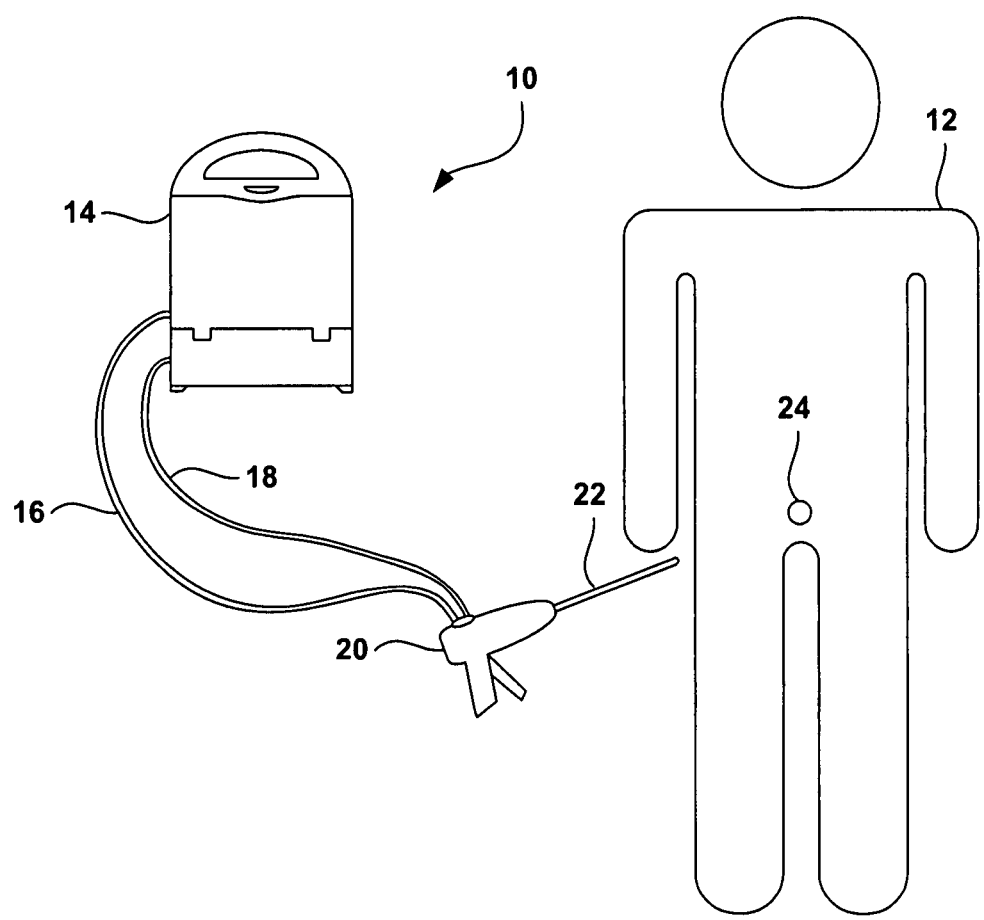
FIG. 1 is a conceptual diagram illustrating an exemplary hand-held device coupled to a generator for treating a patient.

FIG. 1 is a conceptual diagram illustrating an exemplary hand-held device coupled to a generator for treating a patient. As shown in FIG. 1, ablation system 10 may include a portable therapy delivery device (PTD) 14 that delivers therapy to treat a condition of patient 12. In this exemplary embodiment, PTD 14 is a radio frequency (RF) generator that provides RF energy to heat and ablate tissue of the prostate gland 24. The ablation may be accomplished via ohmic heating of the tissue. This ablation of prostate tissue necroses a portion of the enlarged prostate caused by, for example, benign prostatic hyperplasia (BPH). The RF energy is transmitted through electrical cable 16 to hand-held device 20. The energy is then transmitted through a catheter 22 and is delivered to prostate 24 by one or more ablation needle electrodes (not shown). In addition to the ablation needle, a fluid may be pumped out of PTD 14, through tube 18, into hand-held device 20, and through catheter 22 to interact with the RF energy being delivered by the electrode. This wet electrode may increase the effective heating area of the electrode and increase therapy efficacy. Specifically, the effective heating area may be increased or decreased by changing the flow rate of fluid from PTD 14. Alternatively, the shape of the produced lesion may be changed by the type of delivered fluid from the wet electrode or shape and dimensions of the needle electrode. For example, cooled saline or a hypertonic fluid may be used to alter the generally spherical shape of the lesion.

In the illustrated example, PTD 14 includes an RF generator that includes circuitry for developing RF energy from an included rechargeable battery or drawn from a common electrical outlet. The RF energy is produced within defined ablation parameters to provide appropriate prostate tissue heating. PTD 14 also includes a user interface (not shown) that allows a user to control the ablation therapy when the screen of PTD is opened to show the user interface to the user.

Therapy energy and other associated functions such as fluid flow are controlled via the user interface located on a color liquid crystal display (LCD), or equivalent screen. The screen may provide images created by the therapy software, and the user may interact with the software by touching the screen at certain locations indicated by the user interface. In this embodiment, no additional devices, such as a keyboard or pointer device, are needed to interact with the device. The touch screen may also enable device operation.

The touchscreen of the user interface may be a liquid crystal display (LCD) touch screen. The physician may interact with the screen by using a finger or stylus to touch the screen where certain icons appear. In this manner, the physician may control the therapy and PTD operation without the use of additional keyboards or pointer devices. The screen may utilize any type of touch screen technology that allows the physician to select icons or graphics on the screen with a finger, stylus, or gloved finger. These types of technologies include, but are not limited to resistive systems, capacitive systems, and acoustic wave systems.

In some embodiments, the PTD 14 or hand-held device 20 may require an access code or biometric authorization to use the device. Requiring the physician to provide a fingerprint, for example, may limit unauthorized use of the system. In other embodiments, the user interface may include a pointing device, a keyboard, a joystick, or other input device. In alternative embodiments, the user interface may accept verbal commands from the user.

Connected to PTD 14 are one cable 16 and one tube 18. Cable 16 conveys RF energy and tube 18 conducts fluid from PTD 14 to hand-held device 20. Hand-held device 20 may include one or more triggers or levers to extend and retract one or more ablation needle electrodes residing within catheter 22. The triggers are part of a mechanical lever system within the housing of hand-held device 20 which extends and retracts the ablation needles. Hand-held device 20 may also include a button or lever that starts and stops RF energy and/or fluid from PTD 14 from being delivered to patient 12. Alternatively, these types of features may be enabled by the user interface of the PTD 14 instead of on hand-held device 20. Attached to the distal end of hand-held device 20 is a catheter 22. The catheter may provide a conduit for the fluid and house and provide isolation between the one or more ablation needle electrodes that conduct RF energy to patient 12. Fluid may also or instead flow through the one or more ablation needle electrodes. Since catheter 22 would be entering patient 12 through the urethra, the catheter may be very small in diameter and long enough to reach the prostate in any patient needing treatment.

Catheter 22 may contain the one or more needle electrodes for delivering RF current to the tissue of enlarged prostate 24. The needle electrodes of catheter 22 may each penetrate into two areas of prostate 24 from the urethra. The areas may be adjacent to each other or separated into within prostate 24. When RF energy is being delivered, the increase in temperature will ablate a desired volume of tissue. This heating may last a few seconds to a few minutes, depending on the condition of prostate 24 and the desired size of the lesion formed from the ablation therapy. In some embodiments, the fluid may exit small holes in the needles and flow around the electrodes. In other embodiments, the fluid may enter the patient through a different mechanism than holes in the needles. For example, the fluid may pass through a permeable member, along a sheath, or via another element that distributes the fluid in a desired manner. Alternatively, a different catheter or needle than the electrode may deliver the fluid. This conducting fluid, e.g., saline, may increase the effective heating area and decrease the heating time. Additionally, ablating tissue in this manner may enable the physician to complete therapy without repositioning the needle or using different sized needles.

In some cases, hand-held device 20 may only be used for one patient. Reuse may cause infection and contamination, so it may be desirable for the hand-held device to only be used once and then discarded. A feature on the hand-held device may be a smart chip in communication with PTD 14. The smart chip of the device may trigger the processor of PTD 14 to load a specific software application that utilizes the connected hand-hand device 20. As another example, when the hand-held device is connected to PTD 14, the PTD may request use information from hand-held device 20. If hand-held device 20 has been used before, PTD 14 may disable all functions of the hand-held device to prevent reuse of the device on a different patient. This determination may be presented to the user via the user interface as a warning or an error message. The user interface of PTD 14 may suggest a course of action for the user. Once hand-held device 20 has been used, the smart chip in the device may create a use log to identify the therapy delivered and record that the device has been used. The log may include data of RF energy delivered to patient 12, total RF energy delivered in terms of joules or time duration, error messages created, or any other pertinent information. In some embodiments, the user may utilize the user interface to modify the information stored in the log.

In some embodiments, additional peripheral accessories, i.e., therapy devices or diagnostic devices, may be available to the physician at one time. For example, hand-held device 20 for ablating prostate tissue might be coupled with an endoscopic camera for locating the prostate and monitoring therapy. The camera images may then be transferred back to PTD 14 and presented on the screen in real-time. Other examples may include ultrasound imaging coupled with ablation therapy or programming implanted medical devices. The flexible platform of the PTD 14 may allow various diagnostic and therapy combinations to be combined into one device. In these cases, the user interface may be adapted to include these functions within the same delivery screen or require the user toggle between two or more screens to access control or to monitor the additional function.

While PTD 14 is described as a small portable device, the PTD could be embodied as any type of system that supports ablation therapy as described herein. For example, PTD 14 may be an RF generator controlled by a notebook computer. Alternatively, PTD 14 may be a large stationary ablation system that provides a large monitor on top of a stack of components of the system. In other embodiments, PTD 14 may only be the ablation component of a more comprehensive system that supports other functions or therapies separate from the ablation therapy. In any case, PTD 14 is only described herein as an exemplary embodiment of the ablation system which includes the user interface.

Figure 2:
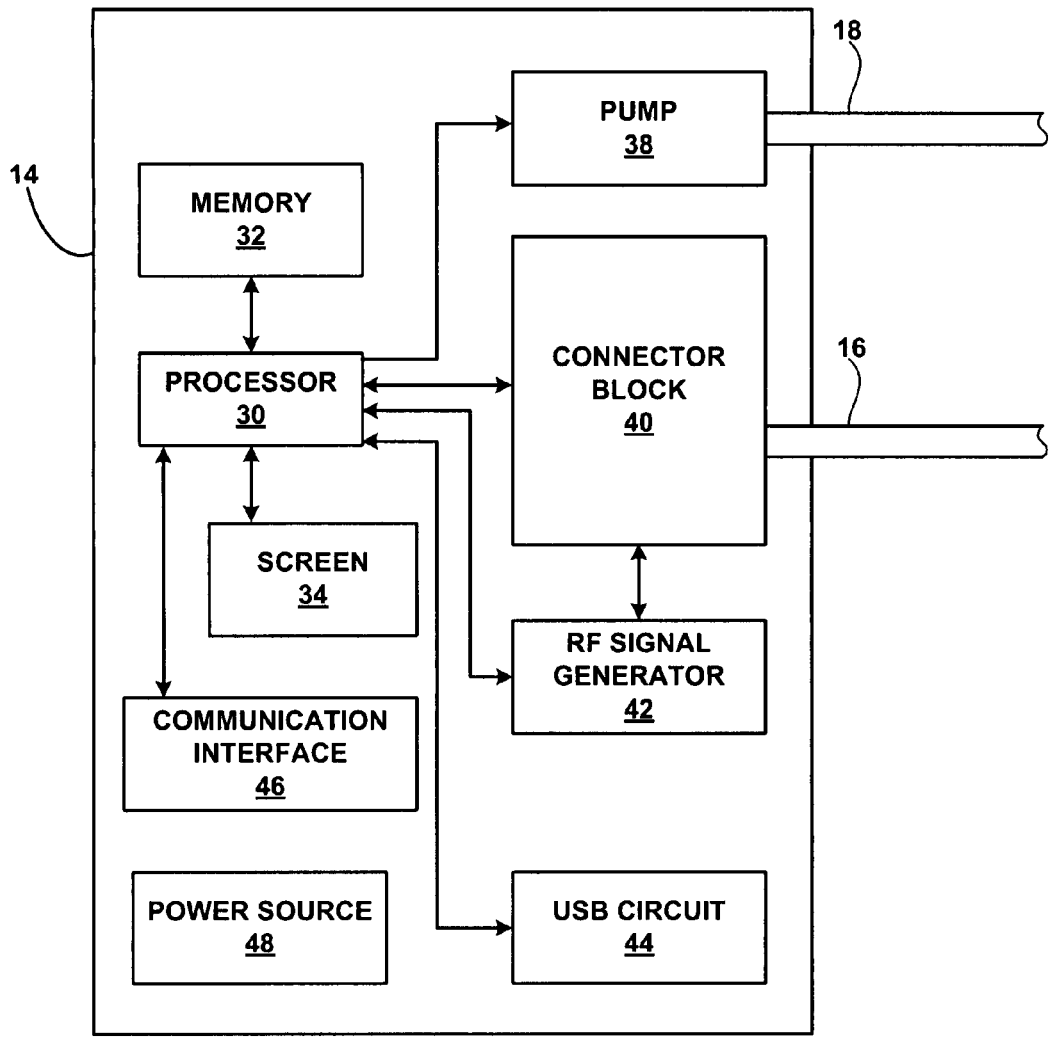
FIG. 2 is a block diagram of the generator that delivers therapy to the patient via the hand-held device.

FIG. 2 is a block diagram of the generator that delivers therapy to the patient via the hand-held device. As shown in FIG. 2, PTD 14 includes a processor 30, memory 32, screen 34, connector block 40, RF signal generator 42, pump 38, communication interface 46, USB circuit 44, and power source 48. As shown in FIG. 2, connector block 40 is coupled to cable 16 for delivering RF energy produced by RF signal generator 42. Pump 38 produces pressure to deliver fluid through tube 18.

Processor 30 controls RF signal generator 42 to deliver RF energy therapy through connector block 40 according to therapy parameter values stored in memory 32. Processor 30 may receive such parameter values from screen 34 or communication interface 46 or USB circuit 44. When signaled by the physician, which may be a signal from the hand-held device 20 conveyed through connector block 40, processor 30 communicates with RF signal generator 42 to produce the appropriate RF energy. As needed, pump 38 provides fluid to irrigate the ablation site or provides fluid to the electrode during wet electrode ablation.

In a preferred embodiment, the RF signal generator may have certain performance parameters. In this exemplary case, the generator may provide RF energy into two delivery channels with a maximum of 50 Watts per channel. Other embodiments may include generation in excess of 100 watts for one channel. Duty cycles of the energy may alter the total power capable of being produced. In other examples, the ramp time for a 50 Watt change in power may occur in less than 25 milliseconds, and the output power may be selected in 1 Watt steps. The maximum current to be provided to the patient may be 2 Amps, and the maximum voltage may be 180 Volts. Other embodiments of the signal generator may have different power capabilities as needed by the intended use of PTD 14.

Connector block 40, e.g. connector board 46, may contain an interface for a plurality of connections, not just the connection for cable 16. These other connections may include one for a return electrode, a second RF energy channel, or a separate temperature sensor. As mentioned previously, connector block 40 may be a variety of blocks used to diagnose or treat a variety of diseases. All connector blocks may be exchanged and connect to processor 30 for proper operation. Pump 38 may be replaceable by the physician to replace a dysfunctional pump or use another pump capable of pumping fluid at a different flow rate.

Processor 30 may also control data flow from the therapy. Data such as RF energy produced, temperature of tissue, and fluid flow may be channeled into memory 32 for analysis. Processor 30 may comprise any one or more of a microprocessor, digital signal processor (DSP), application specific integrated circuit (ASIC), field-programmable gate array (FPGA), or other digital logic circuitry. Memory 32 may include multiple memories for storing a variety of data. For example, one memory may contain therapy parameters, one may contain PTD operational files, and one may contain therapy data. Memory 32 may include any one or more of a random access memory (RAM), read-only memory (ROM), electronically-erasable programmable ROM (EEPROM), flash memory, or the like.

Processor 30 may also send data to USB circuit 44 when a USB device is present to save data from therapy. USB circuit 44 may control both USB ports in the present embodiment; however, USB circuit 44 may control any number of USB ports included in PTD 14. In some embodiments, USB circuit may be an IEEE circuit when IEEE ports are used as a means for transferring data.

The USB circuit may control a variety of external devices. In some embodiments, a keyboard or mouse may be connected via a USB port for system control. In other embodiments, a printer may be attached via a USB port to create hard copies of patient data or summarize the therapy. Other types of connectivity may be available through the USB circuit 44, such as internet access.

Communications with PTD 14 may be accomplished by radio frequency (RF) communication or local area network (LAN) with another computing device or network access point. This communication is possible through the use of communication interface 80. Communication interface 46 may be configured to conduct wireless or wired data transactions simultaneously as needed by a user, e.g., a physician or clinician. In some embodiments, communication interface 46 may be directly connected to connector block 40.

PTD 14 may communicate with a variety of device to enable appropriate operation. For example, PTD may utilize communication interface 46 to monitor inventory, order disposable parts for therapy from a vendor, and download upgraded software for a therapy. In some embodiments, the physician may communicate with a help-desk, either computer directed or human staffed, in real-time to solve operational problems quickly. These problems with PTD 14 or a connected hand-held device may be diagnosed remotely and remedied via a software patch in some cases.

Screen 34 is the interface between PTD 14 and the physician. Processor 30 controls the graphics displayed on screen 34 and identifies when the physician presses on certain portions of the screen 34, which is sensitive to touch control. In this manner, screen 34 operation may be central to the operation of PTD 14 and appropriate therapy or diagnosis.

Power source 48 delivers operating power to the components of PTD 14. Power source 48 may utilize electricity from a standard 115 Volt electrical outlet or include a battery and a power generation circuit to produce the operating power. In other embodiments, power source 48 may utilize energy from any outlet that provides between 100 and 240 Volts. In some embodiments, the battery may be rechargeable to allow extended operation. Recharging may be accomplished through the 115 Volt electrical outlet. In other embodiments, traditional batteries may be used.

In some embodiments, signal generator 42 may be a different type of energy source. For example, the energy source may convert power from power source 48 to produce steam, mechanical energy, or any other type of output that may perform work on patient 12. Other energy may be laser energy or ultrasound energy. In this manner, the energy source may produce electrical, chemical, or mechanical energy.

Figure 3A:
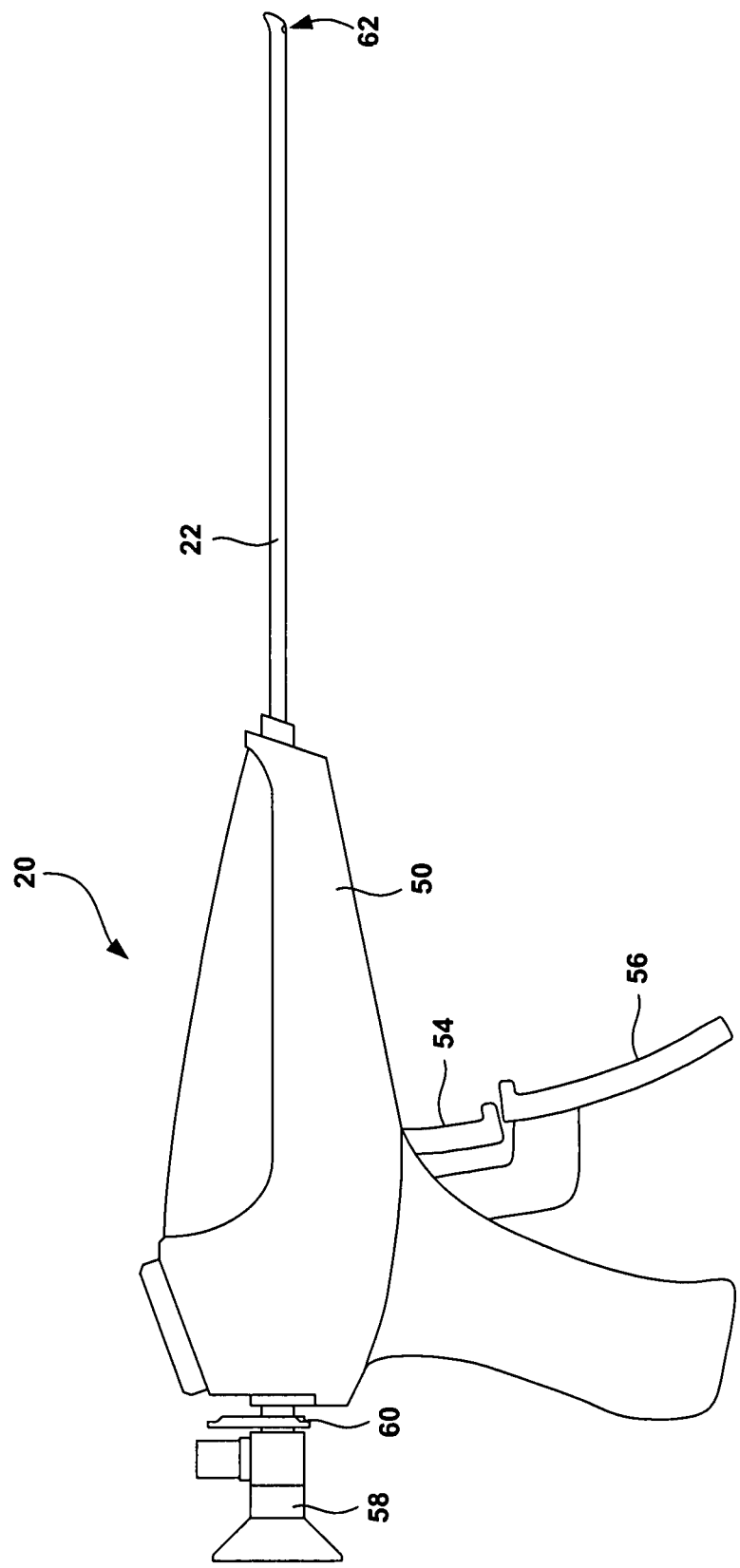
FIG. 3A is a side view of an example hand-held device with a catheter and cystoscope inserted into the catheter.

FIG. 3A is a side view of an example hand-held device with a catheter and cystoscope inserted into the catheter. As shown in FIG. 3A, hand-held device 20 is shown as it would be configured and used by a user to deliver ablation therapy to patient 12. Hand-held device 20 includes housing 50, retraction lever 54, extension lever 56, and sliding lock 60. Cystoscope 58 and catheter 22 are integrated into hand-held device 20 for therapy. Catheter 22 includes port 62 which allows a needle electrode (shown in FIG. 3B) to extend out of the catheter to treat prostate 24 of patient 12.

The user, such as a clinician or physician, inserts cystoscope 58 into a channel of hand-held device 20 and through catheter 22. Cystoscope 58 includes an eye piece, a lens, and a shaft that transmits light from the lens to the eye piece to allow a user to view tissues within patient 12. Once cystoscope 58 is inserted into hand-held device 20, the user slides sliding lock to the closed (locked) position. The portion of cystoscope 58 that remains outside of hand-held device 20 includes an eye piece used to view the image projected from the distal end of catheter 22, through cystoscope 58, and to the eye piece.

Catheter 22 is inserted into the urethra of patient 12 with the aid of a lubricant and local anesthetic. The user holds onto the handle of hand-held device 20 to apply axial pressure to catheter 22 and slide catheter 22 deeper within the urethra of patient 12. The use looks thought cystoscope 58 and out of the distal tip of catheter 22. The user uses cystoscope 58 to identify anatomical landmarks within patient 12 to find the location of prostate 24. Once catheter 22 is correctly positioned adjacent to prostate 24, the user may commence the procedure using levers 54 and 56 and applying RF energy to begin the ablation therapy. As shown, squeezing extension lever 56 against the handle of housing 50 forces the ablation needle to extend out of port 62. Squeezing retraction lever 54 against the handle of housing 50 forces the ablation to retract within port 62. Other example levers or triggers, as described herein, may be used in place of levers 54 and 56.

Figure 3B:
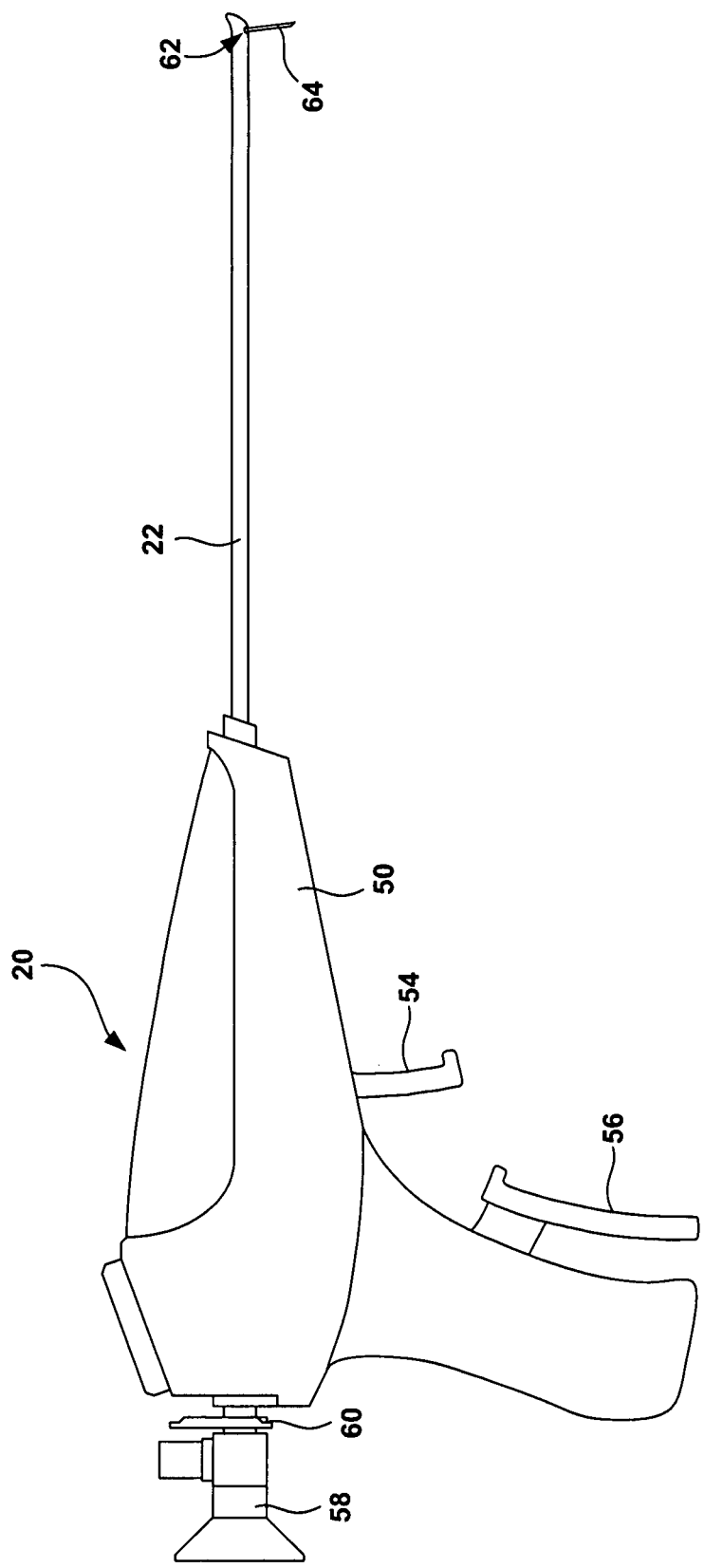
FIG. 3B is a side view of an example hand-held device that extended a needle from the catheter by moving an extension lever.

FIG. 3B is a side view of an example hand-held device 20 that extended a needle from the catheter by moving an extension lever, similar to FIG. 3A. As shown in FIG. 3B, hand-held device 20 has been used by the user to extend needle electrode 64 from port 62. Extension lever 56 has been moved against housing 50 to force needle electrode 64 toward the distal end of catheter 22 and out of port 62. At the same time, retraction lever 54 has moved away from the handle of housing 50 so that the user can squeeze the retraction lever toward the handle of housing 50 to retract needle electrode 64 when the ablation therapy is complete.

In other examples, more than one needle electrode 64 may extend from catheter 22. Each ablation needle that is extended from catheter 22 may extend out from a separate port, similar to port 62. However, multiple needle electrodes 64 may extend from the same port. Multiple needle electrodes 64 may be spaced around the circumference of catheter 22 and/or along the length of catheter 22. While extension lever 56 and retraction lever 54 may be coupled to all needle electrodes, other examples of hand-held device may include multiple extension and retraction levers that are coupled to respective needle electrodes. In this manner, the user may selectively extend a needle electrode from catheter 22 and into patient 12.

Alternative examples of hand-held device 20 may include a mechanical lever system different than levers 54 and 56 shown in FIG. 3B. For example, extension lever 56 may rotate when moved while retraction lever 54 also rotates about respective pivot points within housing 50. Other mechanical lever systems may include a single lever that is moved with respect to housing 50 to perform both extension and retraction functions of the mechanical lever system. In further embodiments, extension lever 56 and retraction lever 54 may be switched in position, placed side by side, or located differently than shown in FIGS. 3A and 3B. These and other examples of hand-held device 20 are described in further detail below.

Figure 4A:
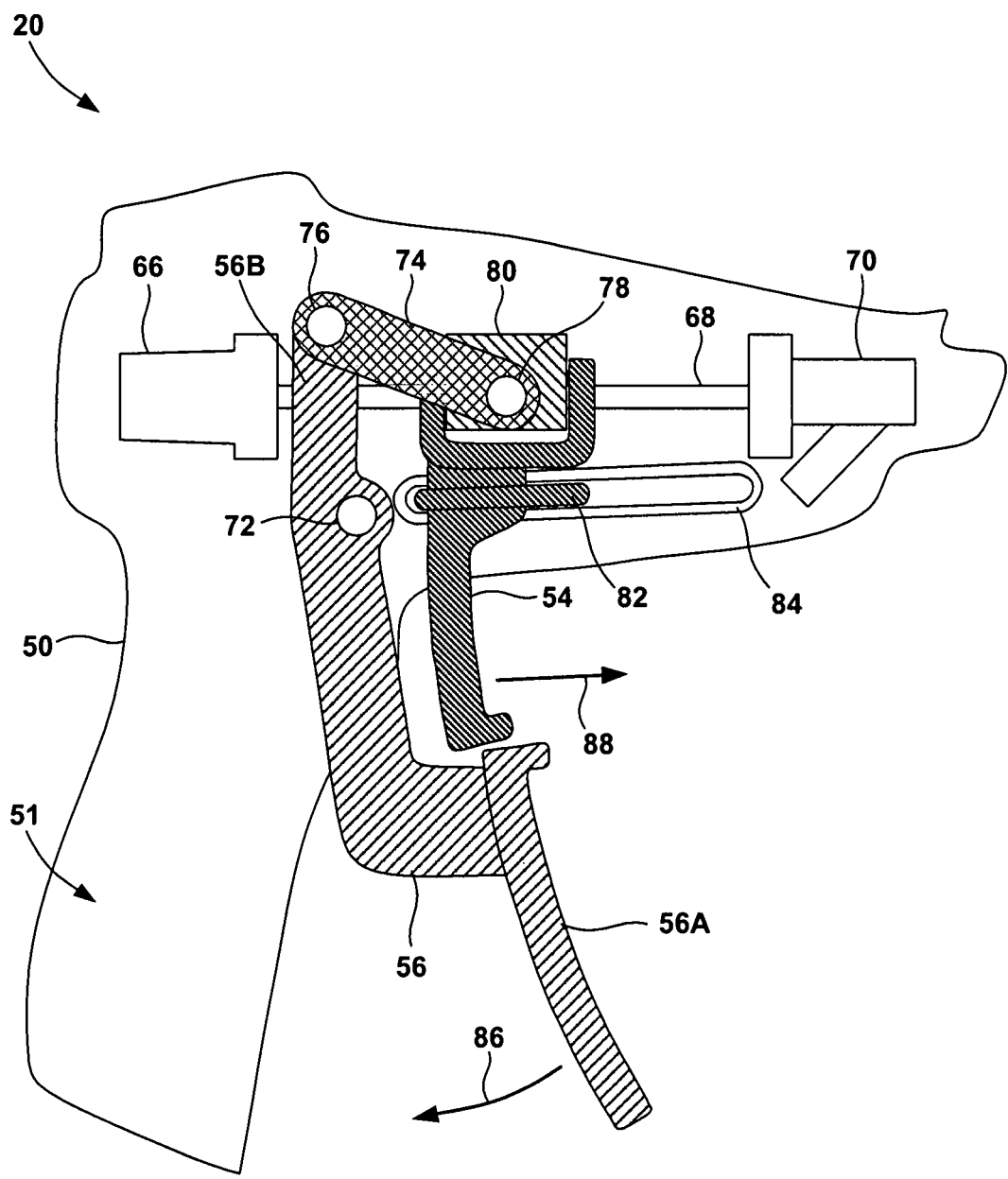
FIG. 4A is a side view of an example hand-held device with an extension lever that pivots and a retraction lever that slides to move a sliding block within the device.

FIG. 4A is a side view of an example hand-held device 20 with an extension lever 56 that pivots and a retraction lever 54 that slides to move sliding block 80 within device 20. As shown in FIG. 4A, hand-held device 20 includes housing 50 that surrounds at least a portion of the components of the hand-held device. Hand-held device 20 includes rear guide 66 and front guide 70 connected by shaft 68. Both rear guide 66 and front guide 70 are fixed to housing 50. Track 84 is also molded into or affixed to housing 50. Extension lever 56 is coupled to sliding block 80 via extension link 74, and retraction lever 54 is directly coupled to the sliding block. Retraction lever 54, extension lever 56, extension link 74, and sliding block 80 are part of the mechanical lever system that includes a rotating element, i.e., extension lever 56, and a linear element, i.e., retraction lever 54. Hand-held device 20 allows the user to always squeeze or move a lever toward handle portion 51 of housing 50 with only one hand in order to perform both the extension of the needle electrode and the retraction of the needle electrode. In alternative examples, shaft 68 may be replaced by a block guide formed into housing 50 or another restraining feature. The block guide may or may not restrict sliding block 80 to linear movement within housing 50. In addition, rear guide 66 and front guide 70 may be formed into housing 50 in other embodiments.

FIG. 4A shows the configuration of hand-held device 20 when the needle electrode (not shown) has not been extended from the catheter. To extend the needle electrode out of housing 50 and the catheter, the user grasps handle portion 51 of housing 50 with the palm of the user's hand and extension lever end 56A with at least one finger. The user then squeezes, e.g., applies a force, the finger against extension lever end 56A in order to move the extension lever in the direction of arrow 86 toward handle portion 51. Extension lever 72 rotates about extension pivot point 72 so that the interior end of the extension lever within housing 50 moves toward front guide 70.

Extension pivot point 74 is a cylinder that is attached to or molded into housing 50. Extension lever end 56B is coupled to extension link 74 via extension link pivot point 76, and the extension link is coupled to sliding block 80 via block pivot point 78. Sliding block 80 includes a channel that at least partially surrounds shaft 68. Therefore, movement of extension lever end 56B toward front guide 70 causes extension link 74 to force sliding block 80 along shaft 68 towards the front guide. Sliding block 80 is coupled to the needle electrode within shaft 68 so that the sliding block moves with the needle electrode.

In addition to the rotational movement of extension lever 56, retraction lever 54 simultaneously moves linearly with sliding block 80 in the direction of arrow 88. Retraction lever 54 includes guide 82 that resides within track 84. Track 84 only allows guide 82, and retraction lever 54, to move in a linear direction according to the configuration of the track. Track 84 may be attached to or molded into housing 50. While track 84 is generally parallel to shaft 68, other examples of hand-held device 20 may position the track at some other non-parallel position with respect to shaft 68. In this case, retraction lever 54 may include a carriage that allows movement of retraction lever 54 with respect to sliding block 80 while retaining the contact between the retraction lever and sliding block 80.

Housing 50 and other components of hand-held device 20 may generally be constructed of metals, polymers, and composite materials. Metals used in the construction of components in hand-held device 20 may include stainless steel, aluminum, an aluminum alloy, titanium, a titanium alloy, or another metal alloy commonly used for hand-held devices. Example polymers may include nylon, polyurethane, high molecular weight polyurethane, polyethylene, polyvinylchloride, or any other polymer. In some examples, components of hand-held device 20 may include one or more different materials to satisfy aesthetic, ergonomic, or functional requirements of the device. In a preferred embodiment, components of hand-held device 20 may be constructed of molded polymers to reduce weight and cost of manufacturing the device. However, components such as extension pivot point 72, extension link pivot point 76, and block pivot point 78 may include metal bushings or another friction reducing component to facilitate movement of the mechanical lever system.

The side view of hand-held device 20 as shown in FIG. 4A only illustrates single pieces of extension lever 56, retraction lever 54, and extension link 74. However, these components may also be located on the other side of shaft 68. For example, extension lever end 56B may split into two ends that straddle shaft 68. These ends of extension lever 56 may each attach to separate extension links on both sides of shaft 68. Each of the two extension links then attach to block pivot points located on opposing sides of sliding block 80. Providing mirror components on both sides of shaft 68 may reduce or eliminate any lateral torque that could be applied to sliding block 80 and affect the extension and retraction of the needle electrode 64 during therapy.

In alternative examples, extension lever 56 may be coupled to sliding block 80 without the use of extension link 74. Instead, extension lever end 56B may be extended to sliding block 80 and include one or more pins that slide along grooves in the side of sliding block. The grooves may be oriented vertically, or substantially perpendicular to the movement of sliding block 80, to allow extension lever end 56B to force the sliding block along shaft 68 while moving with respect to the sliding block. Alternatives such as this may be made to hand-held device 20 and are contemplated herein.

Figure 4B:
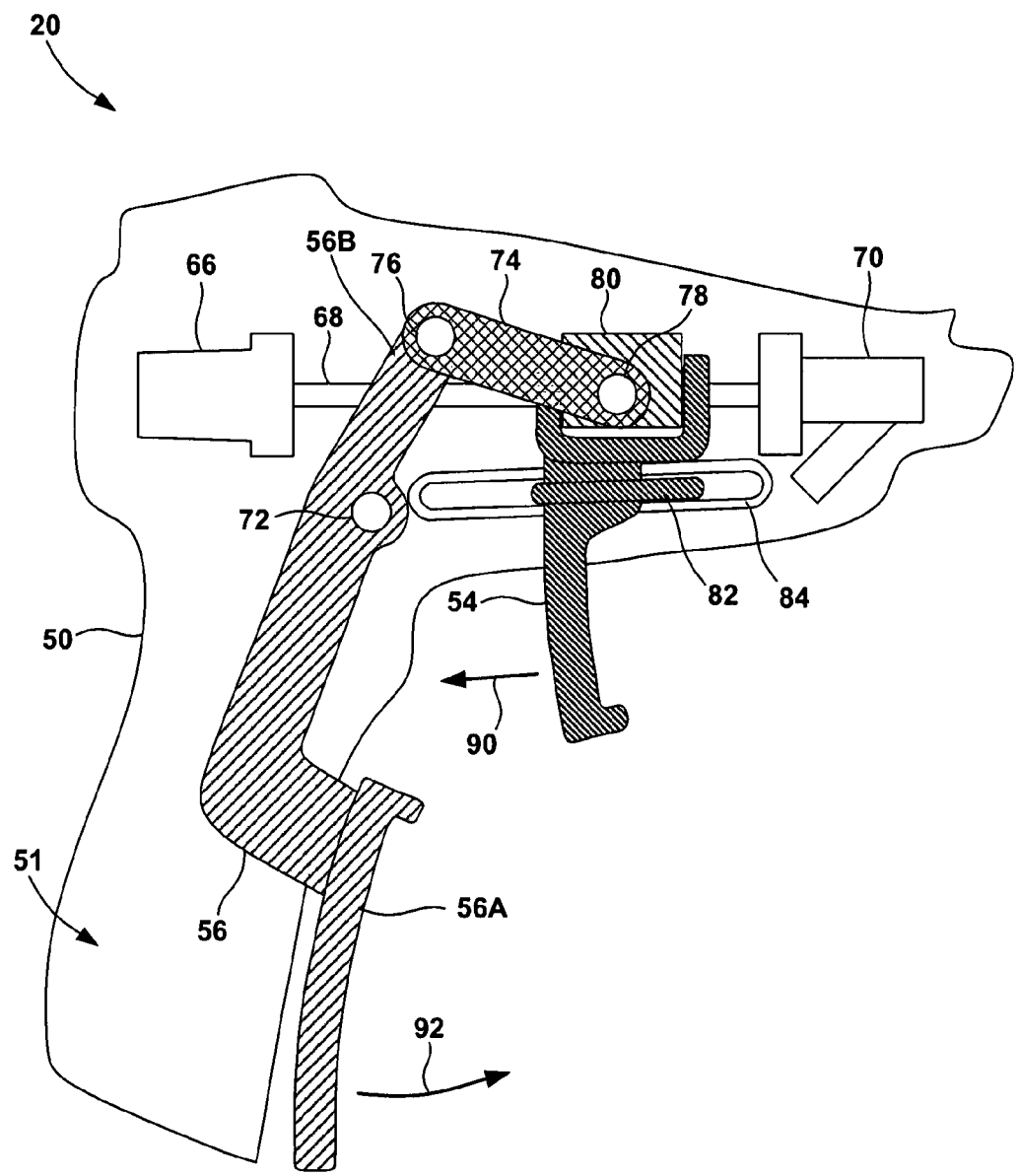
FIG. 4B is a side view of an example hand-held device with an extension lever depressed to move a sliding block forward and extend a needle of the device.

FIG. 4B is a side view of an example hand-held device 20 with an extension lever 56 depressed to move a sliding block 80 forward and extend a needle of device 20. As shown in FIG. 4B, the configuration of hand-held device 20 of FIG. 4A has been altered according to how the mechanical lever system changes when the needle electrode is extended out of the device and the catheter. Specifically, extension lever end 56A has moved toward handle portion 51 and retraction lever 54 has moved forward and away from the handle portion of housing 50. At this location, retraction lever 54 is positioned and ready to be moved toward handle portion 51 and retract the needle electrode 64 back into the catheter.

To retract the needle electrode 64 back into the catheter of hand-held device 20, the user grasps handle portion 51 with the palm of a hand and retraction lever 54 with a finger. The user then applies a force to the retraction lever 54 against handle portion 51 to move the retraction lever in the direction of arrow 90. In turn, retraction lever 54 forces sliding block 80 towards rear guide 66 along shaft 68 to retract the needle electrode 64. Track 84 keeps guide 82 of retraction lever 54 in place during the linear movement of the retraction lever as sliding block 80 is moved.

In addition, retraction lever 54 moving in the direction of arrow 90 causes extension lever 56 to rotate. Sliding block 80 moves toward rear guide 66 and causes extension link 74 to rotate clockwise about block pivot point 78. Extension link 74 pushes extension lever end 56B towards rear guide 66 about extension link pivot point 76. Therefore, extension lever 56 rotates about extension pivot point 72 to move extension lever end 56A in the direction of arrow 92 until hand-held device 20 is in the configuration as shown in FIG. 4A. Hand-held device 20 may move between the configurations of FIGS. 4A and 4B with only one hand of the user as needed to extend and retract the needle electrode 64. The extent of how much sliding block 80 moves along shaft 68 may be limited by bumpers along the shaft, bumpers for the sliding block attached to housing 50, or bumpers which contact one or both of retraction lever 54 and extension lever 56 to stop lever rotation. Alternatively, the bumpers may provide frictional or audible feedback to the user that helps the user monitor the depth of the needle electrode 64 during extension. The feedback may be provided as sliding block 80 passes each distance interval or continuously increasing as the sliding block continues to move.

In alternative embodiments, hand-held device 20 may be configured to rotate shaft 68 and a tool coupled to the shaft. Shaft 68 may be threaded around the outside of the shaft so that the threads couple to guides within the channel of sliding block 80. When sliding block 80 moves linearly from movement of extension lever 56 or retraction lever 54, shaft 68 rotates along with the tool within the shaft. In this manner, the user may user one hand to rotate a tool back and forth with precision. Example applications of translating the linear movement of sliding block 80 to rotational movement of shaft 68 may include tissue tunneling tools, biopsy tools, screw driving tools, implantation or explantation tools, or any other applications that necessitate rotational movement. Additional applications of a threaded shaft 68 may include facilitating calibration of sliding block movement during hand-held device 20 assembly or providing tension feedback to the user during extension and retraction. The tension feedback may be adjustable by the user according to personal preferences.

Figure 5A:
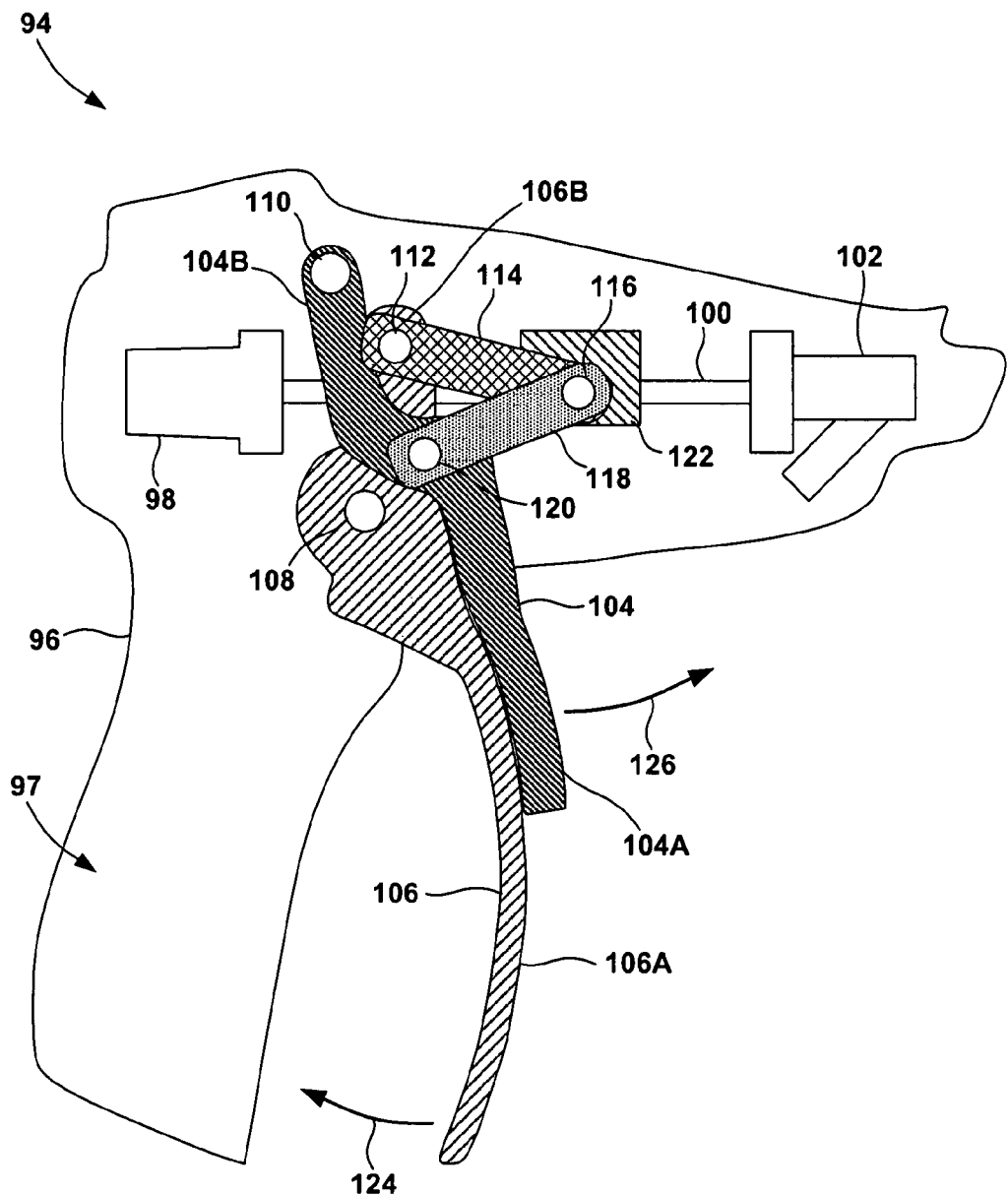
FIG. 5A is a side view of an example hand-held device with an extension lever that pivots and a retraction lever that pivots to move a sliding block within the device.

FIG. 5A is a side view of an example hand-held device 94 with an extension lever 106 that pivots and a retraction lever 104 that pivots to move a sliding block 122 within device 94. As shown in FIG. 5A, hand-held device 94 is an alternative example of hand-held device 20 for extending and retracting an ablation needle electrode 64 for ablation therapy. Hand-held device 94 includes housing 96 that surrounds at least a portion of the components of the hand-held device. Hand-held device 94 includes rear guide 98 and front guide 102 connected by shaft 100. Both rear guide 98 and front guide 102 are fixed to housing 96. Extension lever 106 is coupled to sliding block 122 via extension link 114, and retraction lever 104 is coupled to the sliding block via retraction link 118. Retraction lever 104, retraction link 118, extension lever 106, extension link 74, and sliding block 122 are part of the mechanical lever system that includes two rotating elements, i.e., extension lever 106 and retraction lever 104. Hand-held device 94 allows the user to always squeeze a lever toward handle portion 97 of housing 96 with only one hand in order to perform both the extension of the needle electrode 64 and the retraction of the needle electrode 64.

FIG. 5A shows the configuration of hand-held device 94 when the needle electrode (not shown) has not been extended from the catheter. To extend the needle electrode, such as needle electrode 64, out of housing 96 and the catheter, the user grasps handle portion 97 of housing 96 with the palm of the user's hand and extension lever end 106A with at least one finger. The user then squeezes the finger against extension lever end 106A in order to move the extension lever in the direction of arrow 124 toward handle portion 97. Extension lever 106 rotates about extension pivot point 108 so that extension lever end 106B of the extension lever within housing 96 moves toward front guide 102.

Extension pivot point 108 is a cylinder that is attached to or molded into housing 96. Extension lever end 106B is coupled to extension link 114 via extension link pivot point 112, and the extension link is coupled to sliding block 122 via block pivot point 116. Sliding block 122 includes a channel that at least partially surrounds shaft 100. Therefore, movement of extension lever end 106B toward front guide 102 causes extension link 114 to force sliding block 122 along shaft 100 towards the front guide. Sliding block 122 is coupled to the needle electrode 64 within shaft 100 so that the sliding block moves with the needle electrode 64.

In addition to the rotational movement of extension lever 106, retraction lever 104 rotates in the direction of arrow 126 to move sliding block 122 towards front guide 102. Sliding block 122 moves forward to cause retraction link 118 to rotate clockwise about block pivot point 116. Concurrently, retraction link 118 moves toward front guide 102 and rotates clockwise with respect to retraction link pivot point 120. Retraction link 118 pulls retraction lever end 104A counter-clockwise in the direction of arrow 126. Retraction lever 104 rotates counter-clockwise about retraction pivot point 110 located at retraction lever end 104B. Retraction pivot point 110 is either attached to or formed into housing 96 to allow retraction lever 104 to rotate with respect to housing 96. In this manner, pushing extension lever end 106A toward handle portion 97 causes the extension of the ablation needle electrode 64 out of the catheter and the movement of retraction lever 104 away from the handle portion.

The side view of hand-held device 94 as shown in FIG. 5A only illustrates single pieces of extension lever 106, retraction lever 104, extension link 114, and retraction link 118. However, these components may also be located on the other side of shaft 100. For example, extension lever end 106B may split into two ends that straddle shaft 100. These ends of extension lever 106 may each attach to separate extension links on both sides of shaft 100. Each of the two extension links then attach to block pivot points located on opposing sides of sliding block 122. Additionally, retraction lever end 104B may be split into two ends that straddle shaft 100. The ends of retraction lever 104 may each attach to separate retraction links on both sides of shaft 100. Each of the two extension links then attach to the block pivot points located on the opposing sides of sliding block 122. Providing mirror components on both sides of shaft 100 may reduce or eliminate any lateral torque that could be applied to sliding block 122 and affect the extension and retraction of the needle electrode 64 during therapy.

In alternative examples, one or both of extension lever 106 and retraction lever 104 may be coupled to sliding block 122 without the use of extension link 114 and retraction link 118, respectively. Instead, extension lever end 106B may be extended to sliding block 122 and include one or more pins that slide along grooves in the side of sliding block. The grooves may be oriented vertically, or substantially perpendicular to the movement of sliding block 122, to allow extension lever end 106B to force the sliding block along shaft 100 while moving with respect to the sliding block. Accordingly, retraction lever end 104B may be extended to sliding block 122 and include one or more pins that slide along grooves in the side of sliding block. Sliding block 122 may require one set of grooves for each of extension lever 106 and retraction lever 104. The grooves may be oriented vertically, or substantially perpendicular to the movement of sliding block 122, to allow retraction lever end 104B to force the sliding block along shaft 100 while moving with respect to the sliding block. Alternatives such as this may be made to hand-held device 20 and are contemplated herein.

Figure 5B:
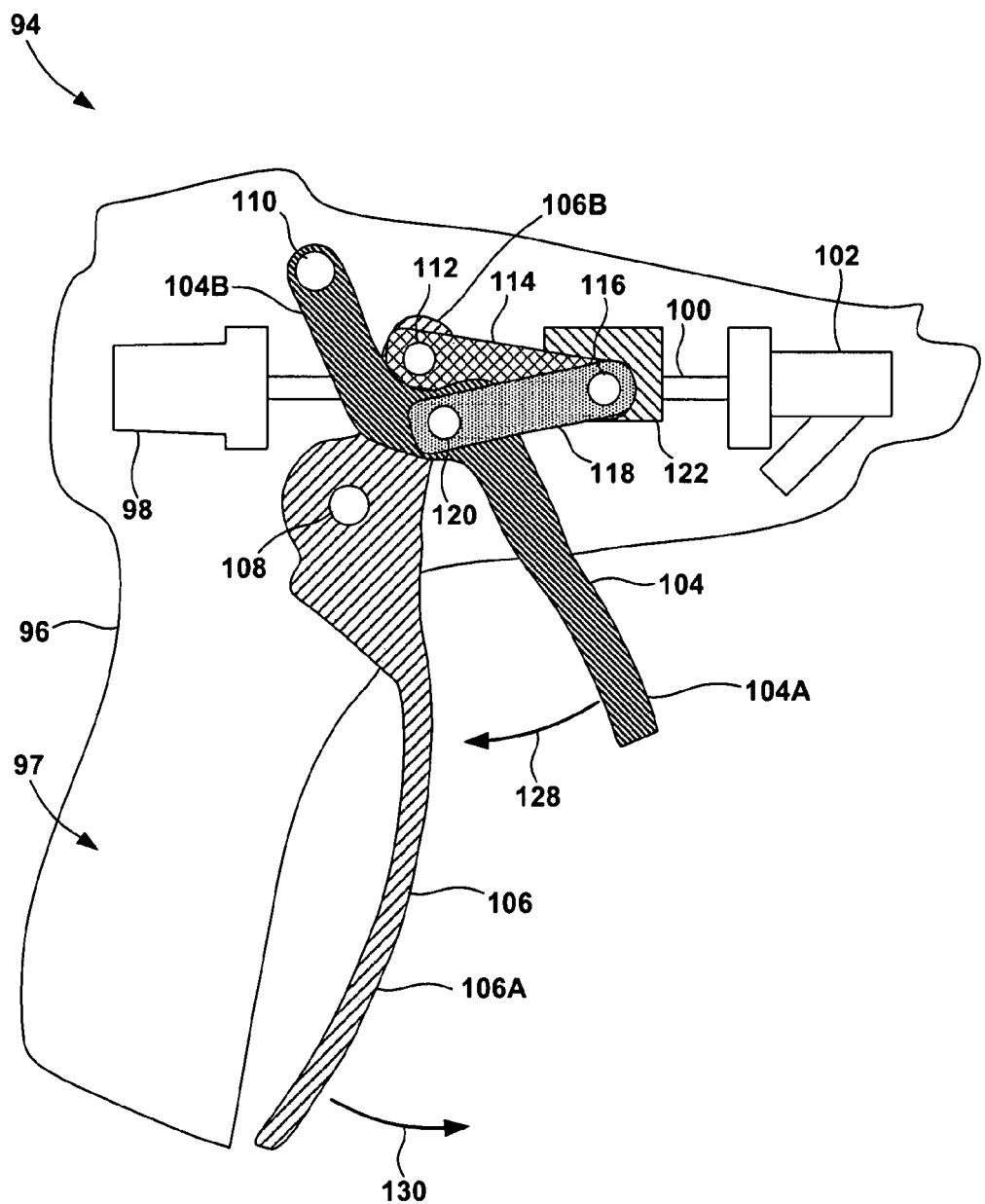
FIG. 5B is a side view of an example hand-held device with an extension lever depressed to move a sliding block forward and extend a needle of the device.

FIG. 5B is a side view of an example hand-held device 20 with an extension lever 106 depressed to move a sliding block 122 forward and extend a needle of device 20. As shown in FIG. 5B, the configuration of hand-held device 94 of FIG. 5A has been altered according to how the mechanical lever system changes when the needle electrode 64 is extended out of the device and the catheter. Specifically, extension lever end 106A has moved toward handle portion 97 and retraction lever 104 has moved forward and away from the handle portion of housing 96. At this location, retraction lever 104 is positioned and ready to be moved toward handle portion 97 and retract the needle electrode 64 back into the catheter.

To retract the needle electrode 64 back into the catheter of hand-held device 94, the user grasps handle portion 97 with the palm of a hand and retraction lever end 104A with a finger. The user squeezes retraction lever 104 against handle portion 97 to rotate the retraction lever in the direction of arrow 128. In turn, retraction lever 104 pulls retraction link 118 toward rear guide 98 and forces sliding block 122 in the same direction along shaft 100 to retract the needle electrode 64. Retraction link 118 rotates counter-clockwise with respect to housing 96 about retraction link pivot point 120 and block pivot point 116.

In addition, retraction lever 104 rotating in the direction of arrow 128 causes extension lever 106 to rotate in the direction of arrow 130 about extension pivot point 108. Sliding block 122 moves toward rear guide 98 and causes extension link 114 to rotate clockwise about block pivot point 116. Extension link 114 pushes extension lever end 106B towards rear guide 98 about extension link pivot point 112. Therefore, extension lever 106 rotates about extension pivot point 108 to move extension lever end 106A in the direction of arrow 130 until hand-held device 94 is in the configuration as shown in FIG. 5A. Hand-held device 94 may move between the configurations of FIGS. 5A and 5B with only one hand of the user as needed to extend and retract the needle electrode 64. The extent of how much sliding block 122 moves along shaft 100 may be limited by bumpers along the shaft, bumpers for the sliding block attached to housing 96, or bumpers which contact one or both of retraction lever 104 and extension lever 106 to stop lever rotation.

Figure 6A:
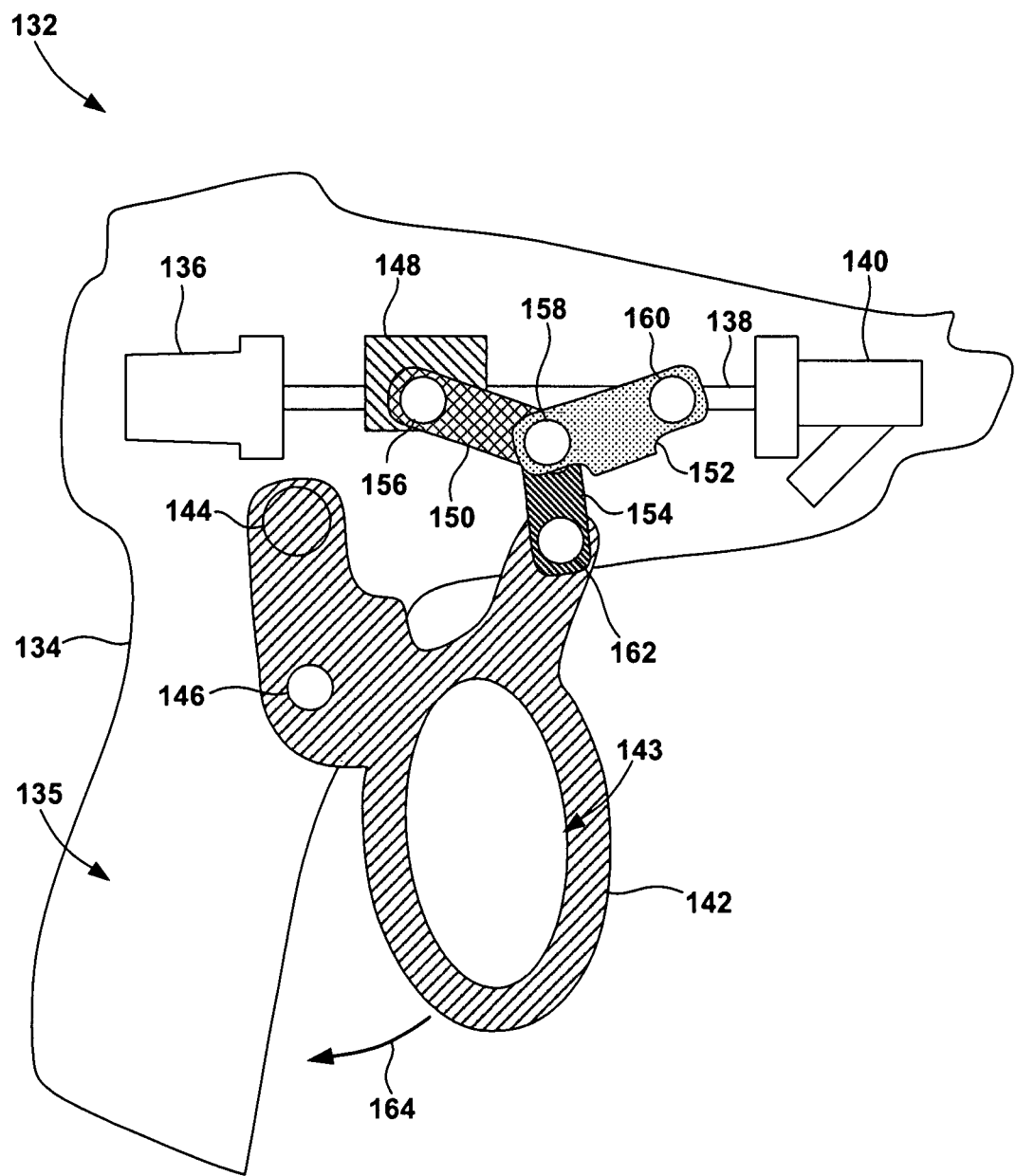
FIG. 6A is a side view of an example hand-held device with a handle that pivots to move a sliding block within the device.

FIG. 6A is a side view of an example hand-held device 132 with a deployment lever 142 that pivots to move sliding block 148 within device 132. Hand-held device 132 is an alternative example of hand-held device 20. As shown in FIG. 6A, hand-held device 132 includes housing 134 that surrounds at least a portion of the components of the hand-held device. Hand-held device 132 includes rear guide 136 and front guide 140 connected by shaft 138. Both rear guide 136 and front guide 140 are fixed to housing 134. Deployment lever 142 is coupled to sliding block 148 via lever link 154 and block link 150. Deployment lever 142 is also coupled to housing 134 via housing link 152 and lever link 154. Deployment lever 142, lever link 154, block link 150 and housing link 152 are part of the mechanical lever system that includes one rotating element, i.e., deployment lever 142. Hand-held device 132 allows the user to squeeze deployment lever 142 toward and away from handle portion 135 of housing 134 with only one hand in order to perform both the extension of the needle electrode 64 and the retraction of the needle electrode 64. In addition, the mechanical lever system of hand-held device 132 may maintain low deployment forces on deployment lever 142 when extending and retracting the needle when compared to other systems described herein. In some examples, hand-held device 132 may also include a thumb hold that extends from handle portion 135 to assist the user in retracting deployment lever 142.

FIG. 6A shows the configuration of hand-held device 132 when the needle electrode (not shown) has not been extended from the catheter. To extend the needle electrode, such as needle electrode 64, out of housing 134 and the catheter, the user grasps handle portion 135 of housing 134 with the palm of the user's hand and deployment lever 142 by placing at least one finger thorough opening 143. The user then squeezes the finger against deployment lever 142 in order to move the deployment lever in the direction of arrow 164 toward handle portion 135. Deployment lever 142 rotates clockwise about lever pivot point 146 so that link pivot point 162 moves generally away from shaft 138. Bumper 144 is formed or added to deployment lever 142 to limit the rotation of the deployment lever with respect to housing 134.

Lever pivot point 146 is a cylinder that is attached to or molded into housing 134. Deployment lever 142 is coupled to lever link 154 via lever link pivot point 162, and lever link 154 is coupled to both block link 150 and housing link 152 via central pivot point 158. Housing link 152 rotates about housing pivot point 160 which is attached to housing 134. In addition, bock link 150 rotates about block pivot point 156 which is attached to sliding block 148. Therefore, rotating deployment lever 142 in the direction of arrow 164 forces lever link 154 to move away from shaft 138, housing link 152 to rotate in a counter-clockwise direction, and block link 150 to rotate in a clockwise direction. In effect, sliding block 148 is pulled toward front guide 140 by block link 150 in order to extend the ablation needle electrode 64 out of hand-held device 132 and the catheter.

The side view of hand-held device 132 as shown in FIG. 6A only illustrates single pieces of lever link 154, housing link 152, and block link 150. However, these components may also be located on the other side of shaft 138. For example, lever link 154, housing link 152, and block link 150 may each consist of two identical elements located on each side of housing 134 and sliding block 148. Providing mirror components on both sides of shaft 138 may reduce or eliminate any lateral torque that could be applied to sliding block 148 and affect the extension and retraction of the needle electrode 64 during therapy.

Figure 6B:
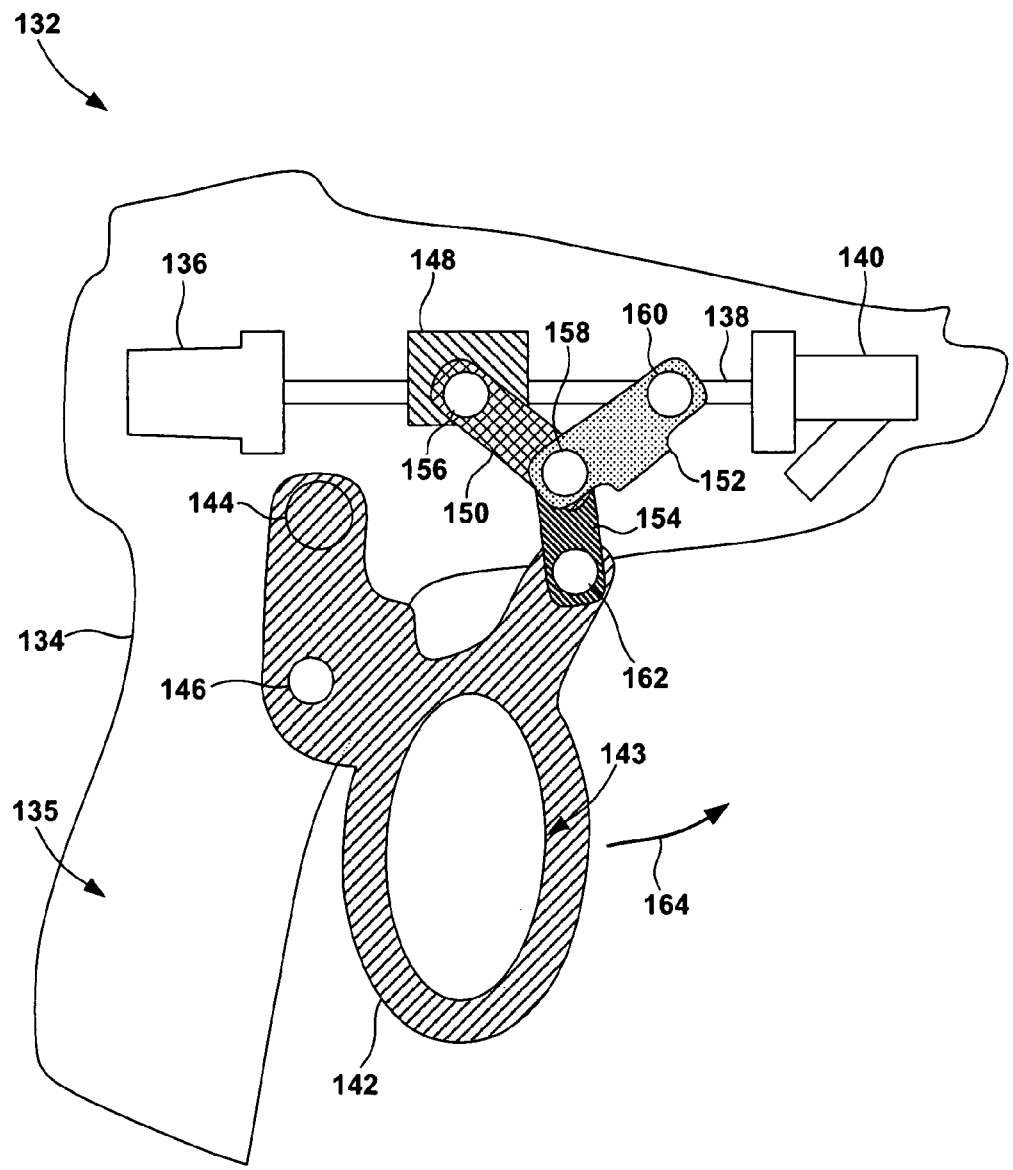
FIG. 6B is a side view of an example hand-held device with a handle that is rotated to pull a sliding block forward within the device.

FIG. 6B is a side view of an example hand-held device 132 with a deployment lever 142 that is rotated to pull sliding block 148 forward within device 132. As shown in FIG. 6B, the configuration of hand-held device 132 of FIG. 6A has been altered according to how the mechanical lever system changes when the needle electrode 64 is extended out of the device and the catheter. Specifically, deployment lever 142 has rotated toward handle portion 135 and sliding block 148 has moved linearly towards front guide 140. At this location, deployment lever 142 is positioned and ready to be moved away from handle portion 135 in order to retract the needle electrode 64 back into the catheter.

To retract the needle electrode 64 back into the catheter of hand-held device 132, the user grasps handle portion 135 with the palm of a hand and deployment lever 142 with one or more fingers through opening 143. The user opens their hand by moving their fingers away from their palm. This action forces deployment lever 142 to rotate away from handle portion 135 in the direction of arrow 164. Therefore, deployment lever 142 pushes lever link 154 toward shaft 138 and lever link 154 in combination with housing link 152 forces block link 150 toward rear guide 136. Block link 150 forces sliding block 148 toward rear guide 136 along shaft 138 to retract the needle electrode 64. Once the user has rotated deployment lever 142 in the direction of arrow 164 so that the needle electrode 64 is retracted, the deployment lever is configured to again extend the needle electrode 64 as shown in FIG. 6A. Hand-held device 132 may move between the configurations of FIGS. 6A and 6B with only one hand of the user as needed to extend and retract the needle electrode 64. The extent of how much sliding block 148 moves along shaft 138 may be limited by bumpers along the shaft, bumpers for the sliding block attached to housing 134, or bumper 144 as described above to stop lever rotation.

Figure 7A:
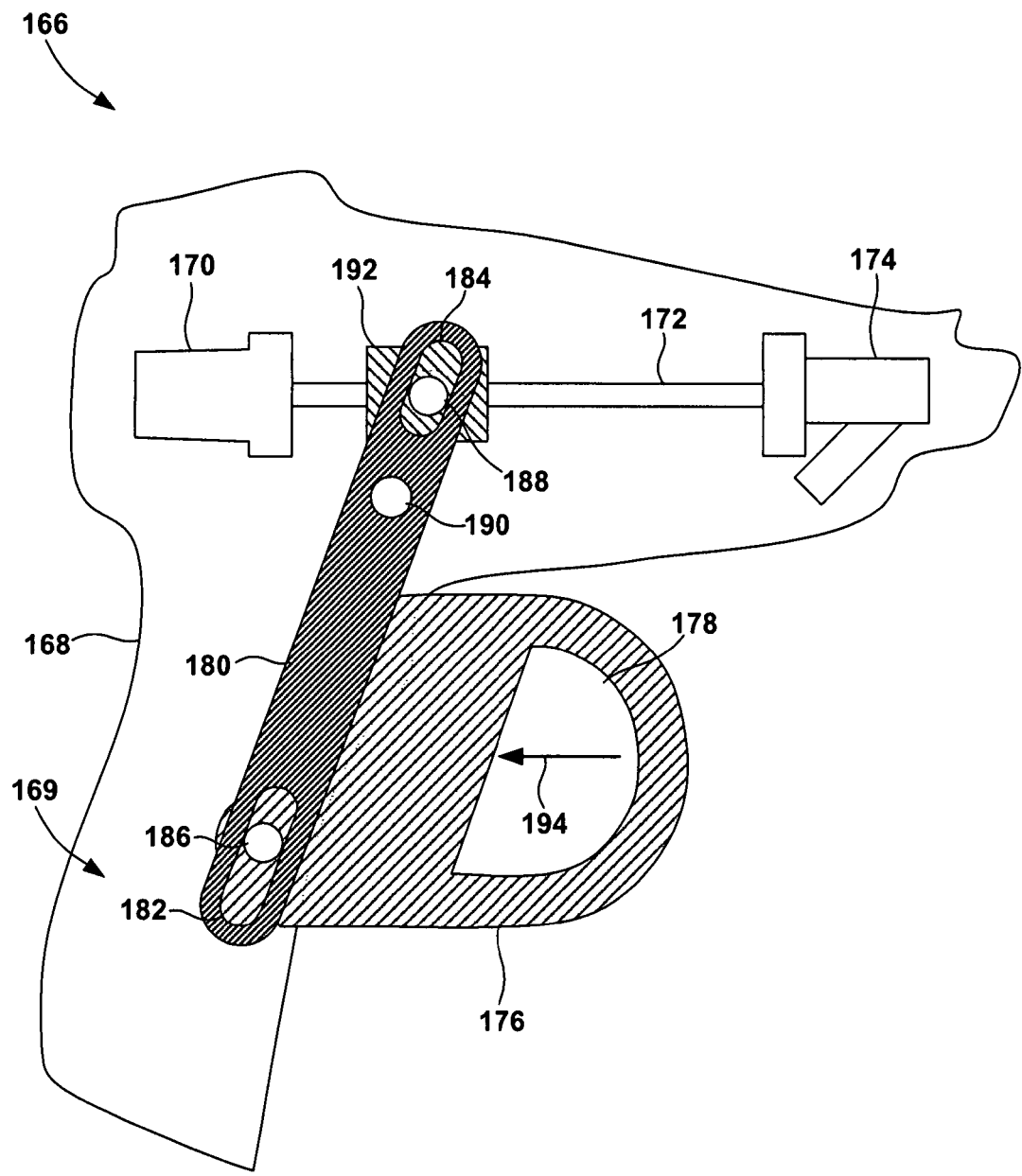
FIG. 7A is a side view of an example hand-held device with a handle that moves linearly against a lever that pivots to move a sliding block within the device.

FIG. 7A is a side view of an example hand-held device 166 with a handle that moves linearly against a deployment lever 176 that pivots to move sliding block 192 within device 166. Hand-held device 166 is an alternative example of hand-held device 20. As shown in FIG. 7A, hand-held device 166 includes housing 168 that surrounds at least a portion of the components of the hand-held device. Hand-held device 166 includes rear guide 170 and front guide 174 connected by shaft 172. Both rear guide 170 and front guide 174 are fixed to housing 168. Deployment lever 176 is coupled to sliding block 192 via lever link 180. Deployment lever 176 is also coupled to housing 168 via linear tracks (not shown) in handle portion 169 of the housing. Deployment lever 176 and lever link 180 are part of the mechanical lever system that includes one rotating element, i.e., link lever 176, and one linear element, i.e., deployment lever 176. Hand-held device 166 allows the user to squeeze deployment lever 176 toward and away from handle portion 169 of housing 168 with only one hand in order to perform both the extension of the needle electrode 64 and the retraction of the needle electrode 64. In some examples, hand-held device 166 may also include a thumb hold that extends from handle portion 169 to assist the user in retracting deployment lever 176.

FIG. 7A shows the configuration of hand-held device 166 when the needle electrode (not shown) has not been extended from the catheter. To extend the needle electrode, such as needle electrode 64, out of housing 168 and the catheter, the user grasps handle portion 169 of housing 168 with the palm of the user's hand and deployment lever 176 by placing at least one finger thorough opening 178. The user then squeezes the finger against deployment lever 176 in order to move the deployment lever linearly in the direction of arrow 164 toward handle portion 169.

Link lever 180 is coupled to deployment lever 176 via link slide 186 within link guide 182. Link lever 180 rotates about link pivot point 190 attached to housing 168. In addition, link lever 180 is coupled to sliding block 192 via block slide 188 within link guide 184. When deployment lever 176 is moved in the direction of arrow 194, link lever 180 rotates clockwise about lever pivot point 190 due to link slide 186 force within link guide 182. Lever pivot point 190 is a cylinder that is attached to or molded into housing 168. Link slide 186 moves away from the center of link lever 180 as the link lever rotates in the clockwise direction. In addition, the clockwise movement of link lever 180 forces link guide 184 against block slide 188 to move sliding block 192 towards front guide 174. Block slide 188 moves away from the center of link lever 180 as the link lever rotates in the clockwise direction. In effect, link lever 180 causes sliding block 192 to slide along shaft 172 and extend the needle electrode 64 out from hand-held device 166 and the catheter.

The side view of hand-held device 166 as shown in FIG. 7A only illustrates single pieces of link lever 180. However, link lever 180 may also be located on the other side of shaft 172. For example, link lever 180 may consist of two identical elements located on each side of housing 168 and sliding block 192. Providing mirror link levers 180 on both sides of shaft 172 may reduce or eliminate any lateral torque that could be applied to sliding block 192 and affect the extension and retraction of the needle electrode 64 during therapy.

Figure 7B:
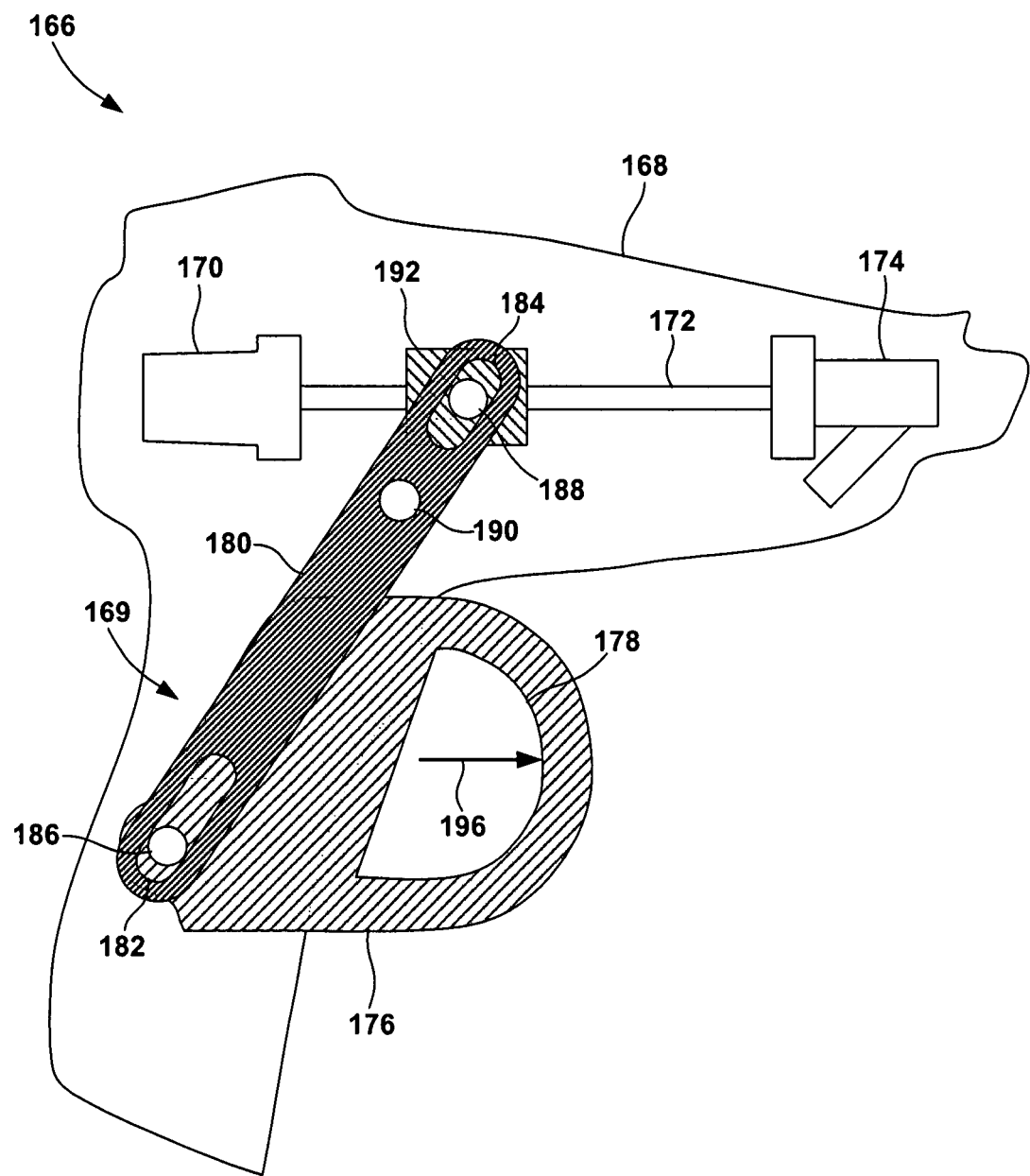
FIG. 7B is a side view of an example hand-held device with a handle that has been moved closer to the handle of the device to force a sliding block forward within the device.

FIG. 7B is a side view of an example hand-held device 166 with a deployment lever 176 that has been moved closer to the handle of the device 166 to force sliding block 192 forward within device 166. As shown in FIG. 7B, the configuration of hand-held device 166 of FIG. 7A has been altered according to how the mechanical lever system changes when the needle electrode 64 is extended out of the device and the catheter. Specifically, deployment lever 176 has been linearly moved towards handle portion 169 of housing 168. In addition, link lever 180 has rotated to move sliding block 192 toward front guide 174. At this location, deployment lever 176 is positioned and ready to be moved away from handle portion 169 in order to retract the needle electrode 64 back in to the catheter.

To retract the needle electrode 64 back into the catheter of hand-held device 166, the user grasps handle portion 169 with the palm of a hand and deployment lever 176 with one or more fingers through opening 178. The user opens their hand by moving their fingers away from their palm. This action forces deployment lever 176 to move linearly away from handle portion 169 in the direction of arrow 196. Therefore, deployment lever 176 forces link lever 180 to rotate counter-clockwise about lever pivot point 190 from the force of link slide 186 against link guide 182. The rotation of link lever 180 creates a force from link guide 184 against block slide 188 in order to move sliding block 192 towards rear guide 170 along shaft 172. In this manner, the movement of sliding block 192 retracts the needle electrode 64 back into the catheter and hand-held device 166, as shown in FIG. 7A. Hand-held device 166 may move between the configurations of FIGS. 7A and 7B with only one hand of the user as needed to extend and retract the needle electrode 64. The extent of how much sliding block 192 moves along shaft 172 may be limited by bumpers along the shaft, bumpers for the sliding block attached to housing 168, or bumpers to stop link lever 180 rotation or deployment lever 176 movement.

Figure 8:
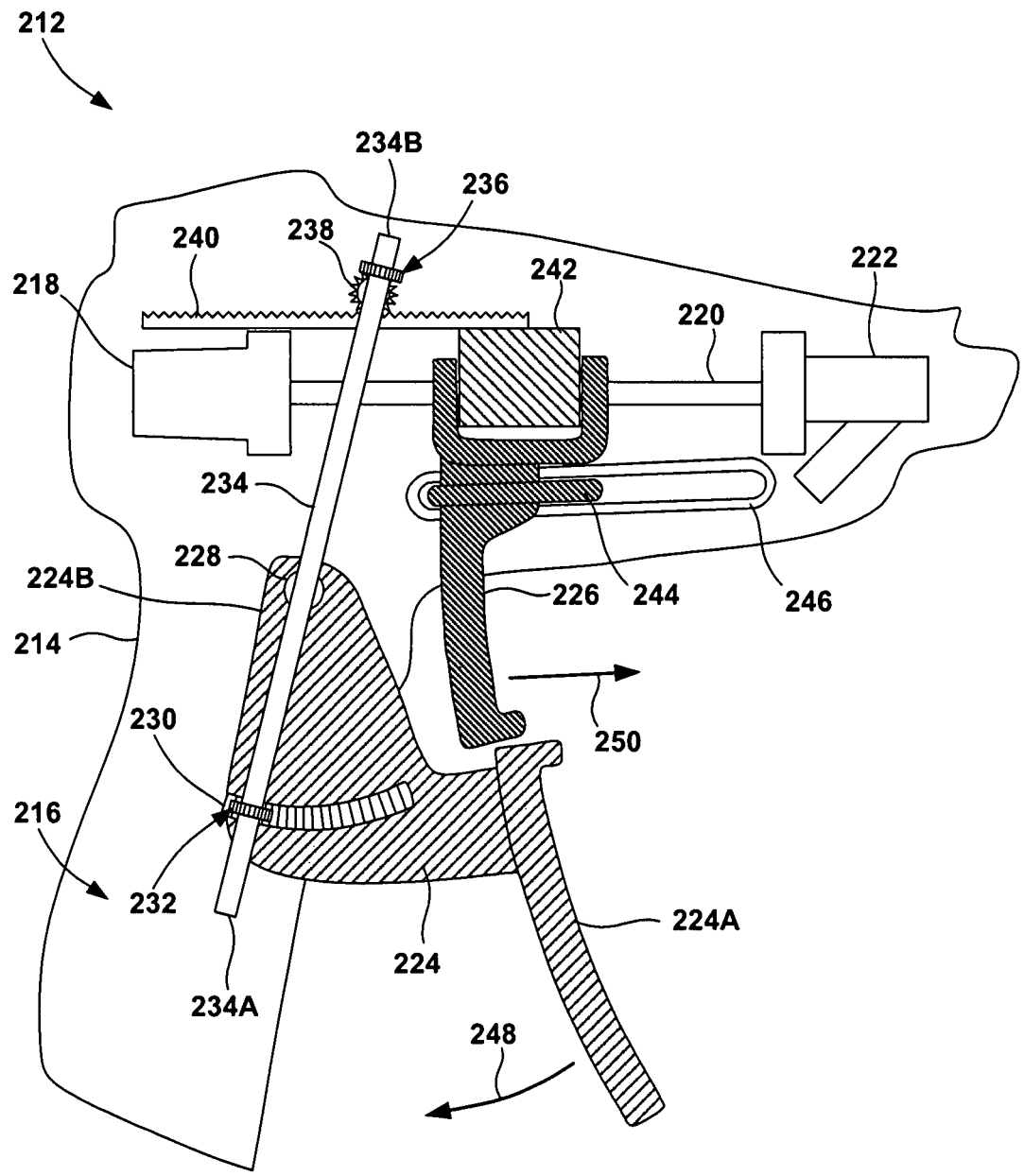
FIG. 8 is a side view of an example hand-held device with an extension lever that pivots and a retraction lever that slides to move a sliding block via a gear system.

FIG. 8 is a side view of an example hand-held device 212 with an extension lever 224 that pivots and a retraction lever 226 that slides to move sliding block 242 via a gear system. As shown in FIG. 8, hand-held device 212 includes housing 214 that surrounds at least a portion of the components of the hand-held device. Hand-held device 212 includes rear guide 218 and front guide 222 connected by shaft 220. Both rear guide 218 and front guide 222 are fixed to housing 214. Track 246 is also molded into or affixed to housing 214. Extension lever 224 is coupled to sliding block 242 via rack 230, shaft 234, and rack 240 that is directly coupled to the sliding block. Retraction lever 226, extension lever 224, extension link racks 230 and 240, gears 232, 236 and 238, and sliding block 242 are part of the mechanical lever system that includes a rotating element, i.e., extension lever 224, and a linear element, i.e., retraction lever 224. The mechanical lever system incorporates elements similar to a "rack and pinion" system to translate motion within hand-held device 212. Hand-held device 212 allows the user to always squeeze a lever toward handle portion 216 of housing 214 with only one hand in order to perform both the extension of the needle electrode 64 and the retraction of the needle electrode 64.

FIG. 8 shows the configuration of hand-held device 212 when the needle electrode (not shown) has not been extended from the catheter. To extend the needle electrode, such as needle electrode 64, out of housing 214 and the catheter, the user grasps handle portion 216 of housing 214 with the palm of the user's hand and extension lever end 224A with at least one finger. The user then squeezes the finger against extension lever end 224A in order to move the extension lever in the direction of arrow 248 toward handle portion 216. Extension lever 224 rotates about extension pivot point 228 so that rack 230 passes by gear 232. Gear 232 contacts teeth of rack 230 such that movement of the rack causes gear 232 and shaft 234 to rotate. Gear 232 is fixed to shaft end 234A.

Rotation of shaft 234 causes gear 236 to rotate at shaft end 234B. Gear 236 contacts teeth of rack 240 to cause the rack to move toward front guide 222 when extension lever end 224A is moved in the direction of arrow 248. Rack 240 is fixed to sliding block 242 to move the sliding block along shaft 220 with rack 240. Accordingly, retraction lever 226 moves with sliding block 242 along track 246 with guide 244 in the direction of arrow 250. Once retraction lever 226 is moved closer to front guide 222, the user may pull against retraction lever 226 to move sliding block 242 back towards rear guide 218 and retract the needle within the cannula and housing 214.

The mechanical lever system shown in hand-held device 212 may be altered to change the magnitude of movement of sliding block 242 with rotation of extension lever 224. Gears 232, 236 and 238, along with racks 230 and 240, may be selected to create gear ratios desired by the user. The gear ratios may be determined so that ergonomically tested rotation of extension lever 224 may correspond to appropriate movement of sliding block 242 and extension of the needle out of the catheter. In addition, more of fewer gears may be used to achieve desired mechanical advantage or orientation of the gears and racks within housing 214.

Figure 9:
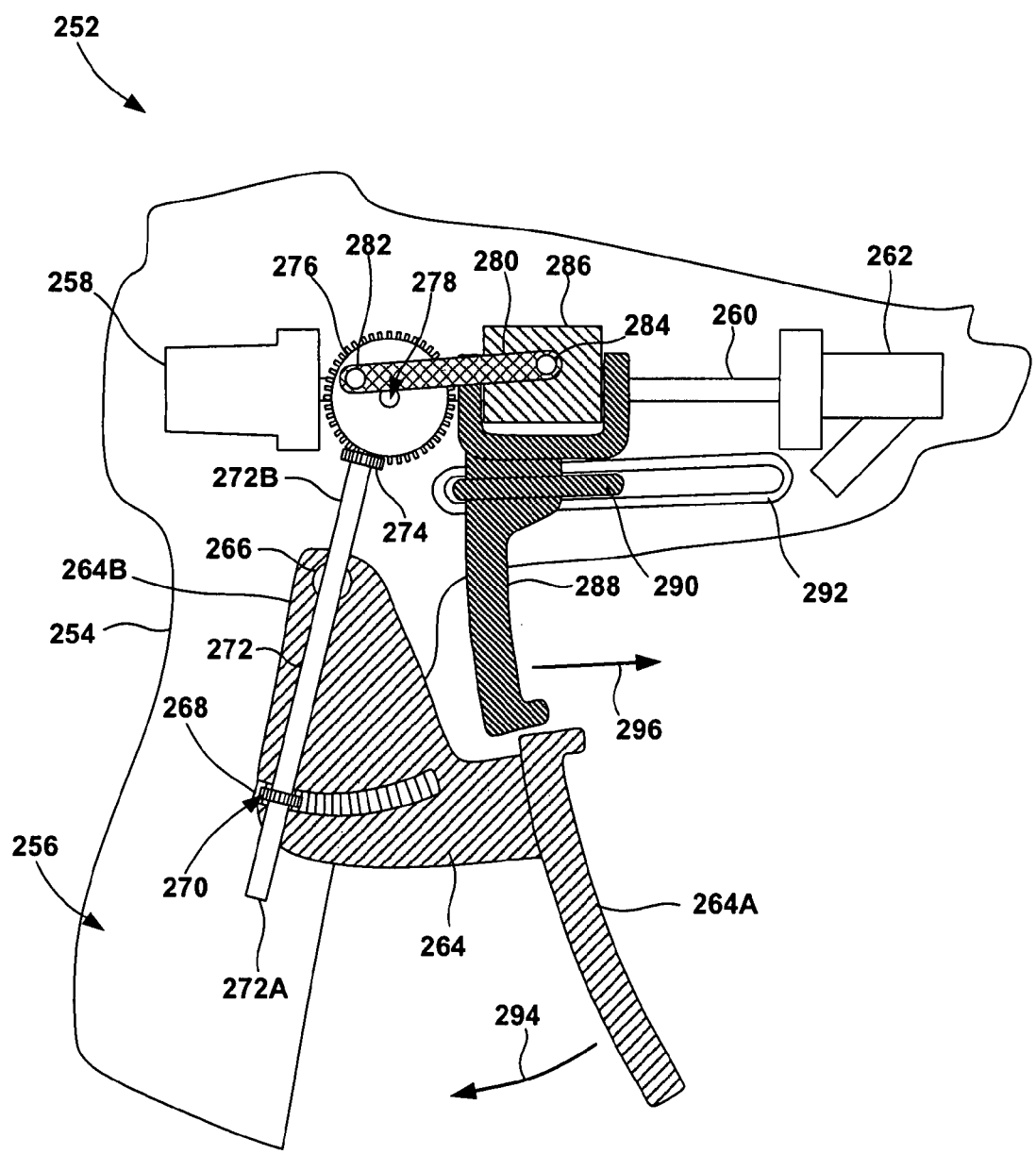
FIG. 9 is a side view of an example hand-held device with an extension lever that pivots and a retraction lever that slides to move a sliding block via a piston system.

FIG. 9 is a side view of an example hand-held device 252 with an extension lever 264 that pivots and a retraction lever 288 that slides to move sliding block 286 via a piston system. As shown in FIG. 9, hand-held device 252 includes housing 254 that surrounds at least a portion of the components of the hand-held device. Hand-held device 252 includes rear guide 258 and front guide 262 connected by shaft 260. Both rear guide 258 and front guide 262 are fixed to housing 254. Track 292 is also molded into or affixed to housing 254. Extension lever 264 is coupled to sliding block 286 via rack 268, shaft 272, gear 276 and block link 280 that is directly coupled to the sliding block. Retraction lever 288, extension lever 264, shaft 272, rack 268, block link 280, gears 270, 274 and 276, and sliding block 286 are part of the mechanical lever system that includes a rotating element, i.e., extension lever 264, and a linear element, i.e., retraction lever 288. The mechanical lever system incorporates elements similar to a "piston" system to translate motion within hand-held device 212, wherein sliding block 286 is the piston. Hand-held device 252 allows the user to always squeeze a lever toward handle portion 256 of housing 254 with only one hand in order to perform both the extension of the needle electrode 64 and the retraction of the needle electrode 64.

FIG. 9 shows the configuration of hand-held device 252 when the needle electrode (not shown) has not been extended from the catheter. To extend the needle electrode, such as needle electrode 64, out of housing 254 and the catheter, the user grasps handle portion 256 of housing 254 with the palm of the user's hand and extension lever end 264A with at least one finger. The user then squeezes the finger against extension lever end 264A in order to move the extension lever in the direction of arrow 294 toward handle portion 256. Extension lever 264 rotates about extension pivot point 266 so that rack 268 passes by gear 270. Gear 270 contacts teeth of rack 268 such that movement of the rack causes gear 270 and shaft 272 to rotate. Gear 270 is fixed to shaft end 272A.

Rotation of shaft 272 causes gear 274 to rotate at shaft end 272B. Gear 274 contacts teeth of gear 276, where gear 276 rotates about gear pivot point 278. Rotation of gear 276 causes link pivot point 282 to move block link 280 towards front guide 262. In turn, block link 280 causes sliding block 286 to move toward front guide 262 along shaft 260. Block link 280 is coupled to sliding block 286 via block pivot point 284. Accordingly, retraction lever 288 moves with sliding block 286 along track 292 with guide 290 in the direction of arrow 296. Once retraction lever 296 is moved closer to front guide 262, the user may pull against retraction lever 288 to move sliding block 286 back towards rear guide 258 and retract the needle within the cannula and housing 254.

The mechanical lever system shown in hand-held device 252 may be altered to change the magnitude of movement of sliding block 286 with rotation of extension lever 264. Rack 268 and gears 270, 274 and 276 may be selected to create gear ratios desired by the user. The gear ratios may be determined so that ergonomically tested rotation of extension lever 264 may correspond to appropriate movement of sliding block 286 and extension of the needle out of the catheter. In addition, more of fewer gears may be used to achieve desired mechanical advantage or orientation of the gears and racks within housing 214.

Figure 10:
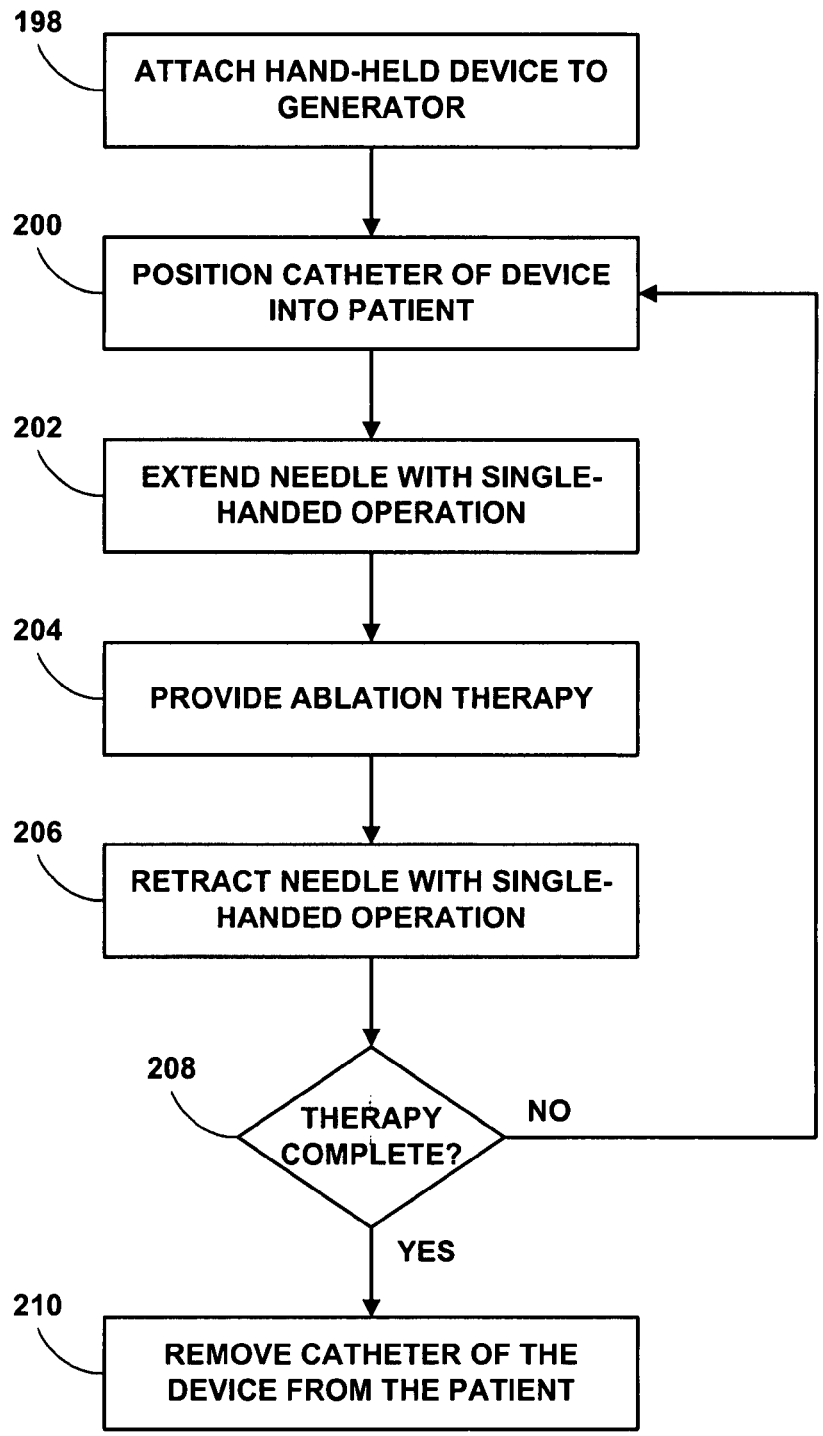
FIG. 10 is a flow diagram illustrating an example technique for treating a patient with a hand-held device coupled to a generator.

FIG. 10 is a flow diagram illustrating an example technique for treating a patient with a hand-held device coupled to a generator. Hand-held device 20 will be used in the example of FIG. 10; however, any of hand-held devices 94, 132, or 166 may be used in a similar manner to perform the ablation therapy. Initially, the user attaches hand-held device 20 to PTD 14 (a generator) with cable 16 and tube 18 (198). Once system 10 is ready for insertion into patient 12, the user slides catheter 22 into the urethra of the patient until the catheter is correctly positioned adjacent to prostate 24 (200). The user then squeezes extension lever 56 with fingers from one hand to extend the needle electrode 64 into prostate 24 (202). The user then initiates ablation therapy by interacting with PTD 14 until a desired lesion has been created in patient 12 (204). In some examples, the user may select the length of needle electrode 64 extension before extending the needle electrode 64 into prostate 24 of patient 12.

When the user has finished creating a lesion via the ablation therapy, the needle electrode 64 may be retracted. The user squeezes retraction lever 54 with fingers from one hand in order to retract the needle electrode 64 back into catheter 22 (206). With the needle electrode 64 retracted into catheter 22, the catheter may be moved in relation to patient 12. If the ablation therapy is not complete (208), the user may rotate catheter 22 within the urethra or slide the catheter to treat a new portion of prostate 24 (200). If the ablation therapy has been completed (208), the user may remove catheter 22 from patient 12 and perform any follow up treatment with the patient (210).

Hand-held device 20, or any other hand-held device 94, 132, or 166, may be restricted to use with only one patient to prevent the transmission of disease between patients. Catheter 22 and/or hand-held device 20 may be disposed of immediately after use. Alternatively, catheter 22 may be disposed while hand-held device 20 is sterilized before being used with a different patient. In any event, hand-held device 20 may be configured to be disposable or sterilized as desired by user 20.

Hand-held devices 20, 94, 132, and 166 have been described herein as being used for the extension of a needle electrode 64 for prostate ablation therapy. However, any hand-held device may be used for other ablation therapies including, but not limited to, cardiac ablation therapy, brain tissue therapy, surgical ablation cutting, or surgical cautery. In addition, the mechanical lever systems of the hand-held devices may be used in other medical applications to extend devices within a patient using a hand-held tool, such as laparoscopic tools or implantation devices. Alternatively, the hand-held devices described herein may be used for applications other than those in the medical field. For example, the mechanical lever systems may be appropriate for use in manufacturing tools, household tools, automotive tools, hobby devices, water hose nozzles, or any other application in which single handed devices may be useful.

The preceding specific embodiments are illustrative of the practice of the invention. It is to be understood, therefore, that other expedients known to those skilled in the art or disclosed herein may be employed without departing from the invention or the scope of the claims. Many embodiments of the invention have been described. Various modifications may be made without departing from the scope of the claims. These and other embodiments are within the scope of the following claims.

The invention claimed is:

1. A device comprising:
a housing configured to be held in a hand of a user;
a sliding element within the housing;
an extension lever coupled to the sliding element;
an extension link that couples the extension lever to the sliding element;
a refraction lever directly coupled to the sliding element;
a track within the housing; and
a guide attached to the retraction lever, wherein the guide slides within the track, wherein:
the extension lever and the refraction lever each extend out from the housing,
the extension lever moves the sliding element and the retraction lever in a first direction when the extension lever is moved in a second direction and the retraction lever moves the sliding element in the second direction when the retraction lever is moved in the second direction,
the extension lever rotates about an extension pivot point of the housing to move the sliding element,
the retraction lever slides linearly with the sliding element,
a first end of the extension link pivots about an extension link pivot point on the extension lever,
the extension link pivot point is different than the extension pivot point, and
a second end of the extension link pivots about a block pivot point attached to the sliding element.

2. The device of claim 1, wherein the sliding element slides linearly along a shaft that resides within a channel of the sliding element, and wherein the shaft remains stationary within the housing when the sliding element slides.

3. The device of claim 1, further comprising a catheter having an ablation needle coupled to the sliding element, wherein:

the extension lever moves in the second direction to extend the ablation needle within the catheter in the first direction; and
the retraction lever moves in the second direction to retract the ablation needle within the catheter in the second direction.

4. The device of claim 3, wherein:
a distal portion of the ablation needle is extended out of the catheter when the extension lever moves in the second direction; and
the distal portion of the ablation needle is retracted back within the catheter when the retraction lever moves in the second direction.

5. A device comprising:
a housing configured to be held in a hand of a user;
a sliding element that moves within the housing;
an extension lever that partially resides within the housing, extends out from the housing, and pivots about an extension pivot point attached to the housing, wherein:
the extension lever is coupled to the sliding element via an extension link;
a first end of the extension link pivots about an extension link pivot point located at a first end of the extension lever and a second end of the extension link pivots about a block pivot point attached to the sliding element; and
the extension pivot point is different than the extension link pivot point; and
a retraction lever that partially resides within the housing, extends out from the housing, and is directly coupled to the sliding element.

6. The device of claim 5, wherein the retraction lever comprises a guide that slides within a track of the housing.

7. The device of claim 5, wherein:
the sliding element and the retraction lever move in a first direction when the extension lever is moved in a second direction; and
the sliding element moves in the second direction and the extension lever moves in the first direction when the refraction lever is moved in the second direction.

8. The device of claim 5, further comprising a catheter having an ablation needle coupled to the sliding element, wherein:
the ablation needle is extended within the catheter in a first direction when the extension lever is moved in a second direction; and
the ablation needle is retracted within the catheter in the second direction when the retraction lever is moved in the second direction.

9. A system comprising:
a generator that produces radio frequency energy for ablation; and
a hand-held device coupled to the generator, wherein the hand-held device comprises:
a housing configured to be held in a hand of a user;
an ablation needle that slides within a catheter coupled to the housing, wherein the ablation needle is coupled to the generator and a sliding element;
an extension lever that extends out from the housing and pivots about an extension pivot point attached to the housing, wherein the extension lever is coupled to the ablation needle and moves the ablation needle in a first direction;
an extension link that couples the extension lever to the sliding element, wherein a first end of the extension link pivots about an extension link pivot point located at a first end of the extension lever and a second end of the extension link pivots about a block pivot point attached to the sliding element, and wherein the extension pivot point is different than the extension link pivot point; and a refraction lever that extends out from the housing, is coupled to the ablation needle, and moves the ablation needle in a second direction, wherein the retraction lever moves with the ablation needle in the first direction when the extension lever is moved in the second direction.

10. The system of claim 9, wherein the retraction lever comprises a guide that slides within a track of the housing.

11. The system of claim 9, wherein the retraction lever pivots about a retraction pivot point at a first end of the retraction lever within the housing, and wherein the retraction pivot point is attached to the housing.

12. The system of claim 11, further comprising a refraction link that couples the retraction lever to the sliding element, wherein a first end of the retraction link pivots about a retraction link pivot point located at a midsection of the retraction lever and a second end of the retraction link that pivots about a block pivot point attached to the sliding element.

13. The system of claim 9, wherein:
the ablation needle is extended from the catheter when the extension lever is moved in the second direction; and
the ablation needle is retracted into the catheter when the retraction lever is moved in the second direction.

14. The system of claim 13, wherein:
the ablation needle does not contact a tissue of a patient when the ablation needle is retracted into the catheter; and
the ablation needle is configured to deliver the radio frequency energy for ablation to the tissue of the patient when the ablation needle is extended from the catheter.

15. The device of claim 1, wherein the hand of the user is a single hand, and wherein both the extension lever and the retraction lever are configured to be operated by the single hand of the user.

16. The system of claim 9, wherein the hand of the user is a single hand, and wherein both the extension lever and the retraction lever are configured to be operated by the single hand of the user.

* * * * *

UNITED STATES PATENT AND TRADEMARK OFFICE
CERTIFICATE OF CORRECTION

| | | |
|---|---|---|
| PATENT NO. | : 8,814,856 B2 | Page 1 of 1 |
| APPLICATION NO. | : 11/799115 | |
| DATED | : August 26, 2014 | |
| INVENTOR(S) | : Ahmed Elmouelhi | |

It is certified that error appears in the above-identified patent and that said Letters Patent is hereby corrected as shown below:

In the Claims

Column 19, line 40: "a refraction lever directly coupled to the" should correctly read -- a retraction lever directly coupled to the --.

Column 19, line 44: "the extension lever and the refraction lever" should correctly read -- the extension lever and the retraction lever --.

Column 19, line 65: "claim 1, further comprising a catheter" should correctly read -- claim 1, further comprising: a catheter --.

Column 20, line 40: "refraction lever is moved in the second" should correctly read -- retraction lever is moved in the second --.

Column 20, line 41: "claim 5, further comprising a catheter" should correctly read -- claim 5, further comprising: a catheter --.

Column 21, line 5: "a refraction lever that extends out from the" should correctly read -- a retraction lever that extends out from the --.

Column 21, line 17: "claim 11, further comprising a refraction link" should correctly read -- claim 11, further comprising: a retraction link --.

Signed and Sealed this
Fourteenth Day of April, 2015

Michelle K. Lee
*Director of the United States Patent and Trademark Office*